(12) United States Patent
Raman et al.

(10) Patent No.: US 12,251,239 B2
(45) Date of Patent: **\*Mar. 18, 2025**

(54) SYSTEM AND METHOD OF ASSESSING INTRA-ARTERIAL FLUID VOLUME USING INTELLIGENT PULSE AVERAGING WITH INTEGRATED EKG AND PPG SENSORS

(71) Applicant: HEMOCEPT INC., Seattle, WA (US)

(72) Inventors: Eric Raman, Seattle, WA (US); Kevin Peterson, Mountain View, CA (US); Iain Hueton, Salt Lake City, UT (US)

(73) Assignee: HEMOCEPT INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/385,294

(22) Filed: Oct. 30, 2023

(65) Prior Publication Data

US 2024/0130692 A1 Apr. 25, 2024
US 2024/0225562 A9 Jul. 11, 2024

Related U.S. Application Data

(63) Continuation of application No. 17/229,741, filed on Apr. 13, 2021, now Pat. No. 11,801,016, which is a
(Continued)

(51) Int. Cl.
*A61B 5/00* (2006.01)
*A61B 5/0205* (2006.01)
(Continued)

(52) U.S. Cl.
CPC .......... *A61B 5/7285* (2013.01); *A61B 5/0006* (2013.01); *A61B 5/0036* (2018.08);
(Continued)

(58) Field of Classification Search
CPC ..... A61B 5/7285; A61B 5/0036; A61B 5/004; A61B 5/024; A61B 5/14; A61B 5/366;
(Continued)

(56) References Cited

U.S. PATENT DOCUMENTS 5,649,543 A 7/1997 Hosaka et al.
5,795,300 A 8/1998 Bryars
(Continued)

FOREIGN PATENT DOCUMENTS

EP 1598004 A1 11/2005
JP 2009-089883 A 4/2009
(Continued)

OTHER PUBLICATIONS

"Oxygen Saturation Measurements from Green and Orange Illuminations of Multi-Wavelength Optoelectronic Patch Sensors, Samah Alharbi, Sijung Hu, David Mulvaney, Laura Barrett, Liangwen Yan, Panagiotis Blanos, Yasmin Elsahar and Samuel Adema, Sensors 2019, 19, 118; doi:10.3390/s19010118".
(Continued)

Primary Examiner — Rex R Holmes
Assistant Examiner — Moussa Haddad
(74) Attorney, Agent, or Firm — MARSHALL, GERSTEIN & BORUN LLP

(57) ABSTRACT

A system using combined electrocardiography (EKG) and photoplethysmography (PPG) sensing to assess intra-arterial fluid volume is described. The system uses averaging of similar pulses based on prior (n–1; n minus 1) R-to-R pulse wave duration, and prior-prior (n–2; n minus 2) R-to-R pulse wave duration, to determine a patient's fluid status and whether it is below or above optimal intravascular hydration.

18 Claims, 33 Drawing Sheets

Related U.S. Application Data continuation of application No. 17/135,936, filed on Dec. 28, 2020.

(60) Provisional application No. 63/067,147, filed on Aug. 18, 2020, provisional application No. 63/009,470, filed on Apr. 14, 2020.

(51) Int. Cl.

| | |
|---|---|
| *A61B 5/022* | (2006.01) |
| *A61B 5/024* | (2006.01) |
| *A61B 5/0245* | (2006.01) |
| *A61B 5/145* | (2006.01) |
| *A61B 5/1455* | (2006.01) |
| *A61B 5/282* | (2021.01) |
| *A61B 5/349* | (2021.01) |
| *A61B 5/366* | (2021.01) |
| *G16H 40/63* | (2018.01) |

(52) U.S. Cl.
CPC ............ *A61B 5/004* (2013.01); *A61B 5/0205* (2013.01); *A61B 5/024* (2013.01); *A61B 5/14* (2013.01); *A61B 5/14552* (2013.01); *A61B 5/282* (2021.01); *A61B 5/349* (2021.01); *A61B 5/366* (2021.01); *A61B 5/4839* (2013.01); *A61B 5/6823* (2013.01); *A61B 5/6831* (2013.01); *A61B 5/6833* (2013.01); *G16H 40/63* (2018.01); *A61B 5/02427* (2013.01); *A61B 5/0245* (2013.01); *A61B 2560/0223* (2013.01); *A61B 2562/146* (2013.01)

(58) Field of Classification Search
CPC ... A61B 5/4839; A61B 5/6823; A61B 5/6831; A61B 5/6833
See application file for complete search history.

(56) References Cited

U.S. PATENT DOCUMENTS

| | | | |
|---|---|---|---|
| 5,913,826 | A | 6/1999 | Blank |
| 6,527,724 | B1 | 3/2003 | Fenici |
| 6,527,728 | B2 | 3/2003 | Zhang |
| 6,805,673 | B2 | 10/2004 | Dekker |
| 7,402,138 | B2 | 7/2008 | Sugo et al. |
| 7,502,643 | B2 | 3/2009 | Farringdon et al. |
| 7,507,207 | B2 | 3/2009 | Sakai et al. |
| 7,674,231 | B2 | 3/2010 | McCombie et al. |
| 7,738,936 | B1 | 6/2010 | Turcott |
| 7,920,919 | B1 | 4/2011 | Nabutovsky |
| 7,941,207 | B2 | 5/2011 | Korzinov |
| 8,447,374 | B2 | 5/2013 | Diab |
| 8,918,153 | B2 | 12/2014 | Cheng |
| 9,031,629 | B2 | 5/2015 | Park et al. |
| 9,060,722 | B2 | 6/2015 | Teixeira |
| 9,254,095 | B2 | 2/2016 | Galloway et al. |
| 9,538,949 | B2 | 1/2017 | Al-Ali et al. |
| 9,700,222 | B2 | 7/2017 | Quinlan et al. |
| 10,010,276 | B2 | 7/2018 | Al-Ali et al. |
| 10,213,123 | B2 | 2/2019 | Hong et al. |
| 10,278,647 | B2 | 5/2019 | Salehizadeh et al. |
| 10,335,044 | B2 | 7/2019 | Banet et al. |
| 10,398,381 | B1 | 9/2019 | Heneghan et al. |
| 10,469,241 | B2 | 11/2019 | Granqvist et al. |
| 10,485,433 | B2 | 11/2019 | Baxi et al. |
| 10,588,554 | B2 | 3/2020 | Poeze et al. |
| 10,624,564 | B1 | 4/2020 | Poeze et al. |
| 2005/0054905 | A1 | 3/2005 | Corl et al. |
| 2006/0142665 | A1 | 6/2006 | Garay et al. |
| 2007/0100219 | A1 | 5/2007 | Sweitzer et al. |
| 2011/0270048 | A1 | 11/2011 | Addison et al. |
| 2013/0066176 | A1 | 3/2013 | Addison et al. |
| 2013/0079606 | A1 | 3/2013 | McGonigle et al. |
| 2014/0100432 | A1 | 4/2014 | Golda et al. |
| 2014/0142445 | A1 | 5/2014 | Banet et al. |
| 2014/0200415 | A1 | 7/2014 | McCombie et al. |
| 2014/0235964 | A1 | 8/2014 | Banet et al. |
| 2014/0276143 | A1 | 9/2014 | Corl |
| 2014/0276145 | A1 | 9/2014 | Banet et al. |
| 2015/0112154 | A1 | 4/2015 | He et al. |
| 2015/0119725 | A1 | 4/2015 | Martin et al. |
| 2015/0182132 | A1 | 7/2015 | Harris et al. |
| 2015/0196257 | A1 | 7/2015 | Yousefi et al. |
| 2015/0282722 | A1 | 10/2015 | Klepp |
| 2015/0313486 | A1 | 11/2015 | Mestha et al. |
| 2016/0007895 | A1 | 1/2016 | Esenaliev et al. |
| 2016/0066863 | A1 | 3/2016 | Thaveeprungsriporn et al. |
| 2016/0148531 | A1 | 5/2016 | Bleich et al. |
| 2016/0360986 | A1 | 12/2016 | Lange |
| 2017/0216706 | A1* | 8/2017 | Bleich ............... A63B 22/0076 |
| 2018/0110432 | A1 | 4/2018 | Nam et al. |
| 2018/0279891 | A1 | 10/2018 | Miao et al. |
| 2018/0303355 | A1 | 10/2018 | McCombie et al. |
| 2018/0344177 | A1 | 12/2018 | Banet et al. |
| 2018/0351120 | A1 | 12/2018 | Bao et al. |
| 2018/0360325 | A1 | 12/2018 | Robinson et al. |
| 2019/0059752 | A1 | 2/2019 | Botsva et al. |
| 2019/0076097 | A1 | 3/2019 | Edouard |
| 2019/0110363 | A1 | 4/2019 | Bao et al. |
| 2019/0167130 | A1 | 6/2019 | Marchand et al. |
| 2019/0183422 | A1 | 6/2019 | Moon et al. |
| 2019/0216396 | A1 | 7/2019 | McCombie et al. |
| 2019/0229371 | A1 | 7/2019 | Song et al. |
| 2019/0254524 | A1 | 8/2019 | Granqvist et al. |
| 2019/0254540 | A1 | 8/2019 | Banet et al. |
| 2020/0093389 | A1 | 3/2020 | Henry et al. |
| 2020/0138316 | A1 | 5/2020 | Galloway et al. |
| 2020/0163558 | A1 | 5/2020 | Baxi et al. |

FOREIGN PATENT DOCUMENTS

| | | |
|---|---|---|
| WO | WO-1998025516 A1 | 6/1998 |
| WO | WO-2006023924 A1 | 3/2006 |
| WO | WO-2014/011368 A1 | 1/2014 |
| WO | WO-2014042845 A1 | 3/2014 |
| WO | WO-2017/217599 A1 | 12/2017 |
| WO | WO-2020/254882 A1 | 12/2020 |

OTHER PUBLICATIONS

A-H, Tsai T-H, et al. (2016) Modeling the Pulse Signal by Wave-Shape Function and Analyzing by Synchrosqueezing Transform. PLoS One 11(6): e0157135. doi:10.1371/journal.pone.0157135.

Ability of esCCO to track changes in cardiac output, M. Biais, R. Berthezene, L. Petit, V. Cottenceau and F. Sztark, British Journal of Anaesthesia, 2015, 403-10 doi 10.1093/bja/aev219.

Ambulatory Pulse Wave Velocity Monitoring: A Step Forward, DOI: 10.1161/HYPERTENSIONAHA.117.09121.), 2017 American Heart Association, Inc.

Comparison between continuous non-invasive estimated cardiac output by pulse wave transit time and thermodilution method, Ashish C. Sinha, Preet Mohinder Singh, Navneet Grewal, Mansoor Aman, Gerald Dubowitz, Annals of Cardiac Anaesthesia vol. 17:4 Sep.-Dec. 2014.

Continuous Estimation of Cardiac Output in Critical Care: A Noninvasive Method Based on Pulse Wave Transit Time Sompared with Transpulmonary Thermodilution, Ulrike Ehlers, Rolf Erlebach, Giovanna Brandi, Federica Stretti, Richard Valek, Stephanie Klinzing, and Reto Schuepbach, Critical Care Research and Practice vol. 2020, Article ID 8956372, 7 pages ttps://doi.org/10.1155/2020/8956372.

Cox et al., Investigation of photoplethysmogram morphology for the detection of hypovolemic states, Engineering in Medicine and Biology Society, 30th Annual International Conference of the IEEE, 5486-5489 (Aug. 2008).

Cuff-Free Blood Pressure Estimation Using Pulse Transit Time and Heart Rate, Ruiping Wang, Wenyan Jia, Zhi-Hong Mao, Robert J. Sclabassi, and Mingui Sun, Int Conf Signal Process Proc. Oct. 2014 ; 2014: 115-118. doi:10.1109/ICOSP.2014.7014980.

(56) References Cited

OTHER PUBLICATIONS

Design and-Prototyping of a Wristband-I ype Wireless Photoplethysmographic Device Mr Heart-Rate Variability Signal analysis, M. Ghamari, Department of Electrical and Computer Engineering, University of Texas at El Paso, El Paso, Texas, USA Sonf Proc IEEE Eng Med Biol Soc. Author manuscript; available in PMC Sep. 26, 2017.
Development of a Low-CostWireless Phonocardiograph With a Bluetooth Headset under Resource-Limited Conditions, Himel Mondal, Shaikat Mondal and Koushik Saha, Med. Sci. 2018, 6, 117; doi:10.3390/medsci6040117.
Eko DUO ECG + Digital Stethoscope, https://www.hopkinsmedicalproducts.com/electronic-stethoscopes.
European Patent Application No. 21788309.9, Extended European Search Report, dated Jan. 22, 2024.
European Patent Application No. 21788382.6, Extended European Search Report, dated Jan. 25, 2024.
Evaluation of pulse wave transit time analysis for non-invasive cardiac output quantification in pregnant patients Emmanuel Schneck, Pascal Drubel, Rainer Scharg, Melanie Markmann, Thomas Kohl, Scientific Reports I (2020) 10:1857 I https://doi.org/10.1038/s41598-020-58910-x Michael Henrich, Michael Sander & Christian Koch.
Evaluation otlVliniature Wireless War-Signs Monitor in a I rauma Intensive Care Unit, Jonathan P. Meizoso, MD; Casey J. Allen, MD; Juliet J. Ray, MD; Robert M. Van Haren, MD, MSPH; F. Teisch BS-Xiomara Ruiz Baez, MD; Alan S. Livingstone, MD; Nicholas Namias, Md, MBA; Carl I. Schulman, MD, PhD, MSPH; Kenneth G. Proctor, PhD, Military Medicine, vol. 181, May Supplement 2016.
Extraction of respiratory signals from the electrocardiogram and photoplethysmogram: echnical and physiological determinants; Peter H Charlton et al 2017 Physiol. Meas. 38 669.
International Application No. PCT/US21/27158, International Search Report and Written Opinion, mailed Aug. 10, 2021.
International Application No. PCT/US21/27161, International Search Report and Written Opinion, mailed Aug. 20, 2021.
Marks et al., Stockwell Transform Detector For Photoplethysmography Signal Segmentation, 52nd Asilomar Conference on Signals, Systems and Computers, IEEE, 1239-1243 (Oct. 2018).
Novel Methods for Pulse Wave Velocity Measurement, Tania Pereira, Carlos Correia, Joao Cardoso, J. Med. Biol. Eng. (2015) 35:555-565, JOI 10.1007/s40846-015-0086-8.
Photoplethysmography for Quantitative Assessment of Sympathetic Nerve Activity (SNA) During Cold Stress, https://www.frontiersin.org/articles/10.3389/fphys.2018.01863/full.
PPG and ECG feature comparison for healthy people and hypertensive patients, Jan. 2012 D01:10.1109/BH1.2012.6211701.
Precision wearable accelerometer contact microphones for longitudinal monitoring of mechano-acoustic ardiopulmonary signals, Pranav Gupta, Mohammad J. Moghimi, Yaesuk Jeong, Divya Gupta, Omer T. Irian and Farrokh Ayazi npj Digital Medicine vol. 3, Article No. 19 (2020).
Pulmonary Artery Catheterization, 2020 Up To Date, Inc.
Pulse oximetry, 2020 Up To Date, Inc.
Pulse Oximetry, Book Chapter.
Pulse oximetry: Understanding its basic principles facilitates appreciation of its limitations, Edward D. Chan, Michael M. Chan, Mallory M. Chan, Respiratory Medicine (2013) 107, 789e799.
Pulse Transit Time and Blood Pressure During Cardiopulmonary Exercise Tests T Wibmer, K. Doering, C. Kropf-Sanchen, S. Rudiger, I. Blanta, K. M. Stoiber, W. Rottbauer, C. Schumann, Department of Internal Medicine II, University Hospital of Ulm, Ulm, Germany, Received May 29, 2013, Accepted govember 29, 2013, On-line Feb. 24, 2014.
Real-time aortic pulse wave velocitymeasurement during exercise stress testing, Pau A. Roberts, Brett R. Cowan, Yingmin Liu, Aaron C. W. Lin, Poul M. F. Nielsen, Andrew J. Taberner, Ralph A. H. Stewart, Hai leng Lam and Alistair A. Young,Roberts et al. Journal of Cardiovascular Magnetic Resonance (2015) 17:86; DOI 10.1186/s12968-015-0191-4.
Reflectance pulse oximetry: Practical issues and limitations, Hooseok Lee, Hoon Ko, Jinseok Lee, ScienceDirect CT Express 2 (2016) 195-198.
Shafqat et al., Estimation of instantaneous venous blood saturation using the photoplethysmograph (PPG) waveform, Physiological Measurement, 36(10):1-14 (2015).
Standard Terminologies for Photoplethysmogram Signals, DOI: 10.2174/157340312803217184.
Towards Ubiquitous Blood Pressure Monitoring via Pulse Transit Time: Theory and Practice, Ramakrishna Mukkamala, EEE Trans Blamed Eng. Author manuscript; available in PMC Aug. 1, 2015.
Vahdani-Manaf, Development of novel physiological analysis methods based on dual-wavelength photoplethysmographic signals time differences, J. Medical Imaging and Health Informatics, 6(2):372-9 (Apr. 2016).
Wearable Solutions For Improving Heart Health and Wellness PPG vs. ECG-based Biosensors: The Pros and Cons NeuroSky.

\* cited by examiner

Select, based on:

prior RtoR = $RtoR_{n-1}$
or
prior-prior RtoR = $RtoR_{n-2}$

↓

Multiple Pulse Data Sets. PPG signals for each wavelength are averaged and a Composite Pulse Data Set is constructed with the new PPG signal data for each wavelength

→

1001　1002
↓　　↓ red composite pulse, count = 8, prior_r2r = 0.898

$PPGSignal_{Red}$ ir composite pulse, count = 8, prior_r2r = 0.898

$PPGSignal_{IR}$ green composite pulse, count = 8, prior_r2r = 0.898

$PPGSignal_{Green}$ 0.0　0.5　1.0　1.5　2.0　2.5

↓

$PPGSignal_{Red, IR, Green}[t \geq t0_n]$ :

$SPOS_{Red, IR, Green}[t \geq t0_n]$ :

$PWTT_{Red, IR, Green} = t_{SPOSmin} - t0_n$ :

Composite Pulse Data Set

FIG. 10

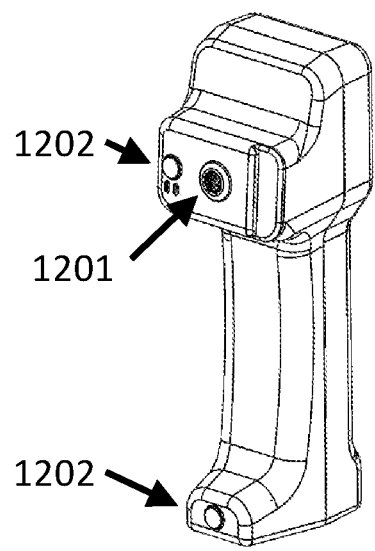
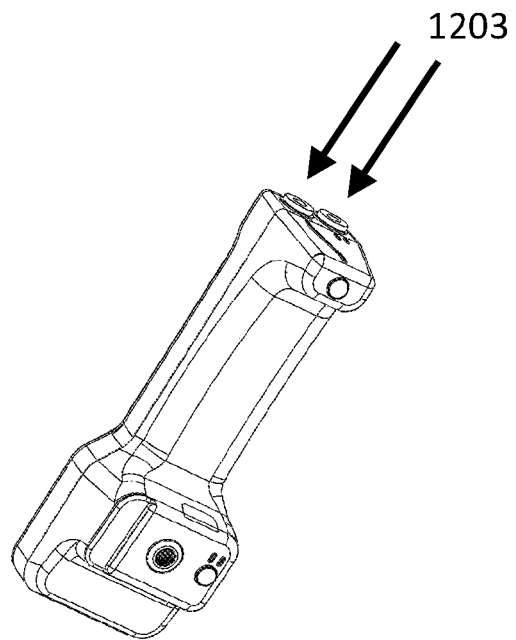
FIG. 12A　　　　　　　　　FIG. 12B
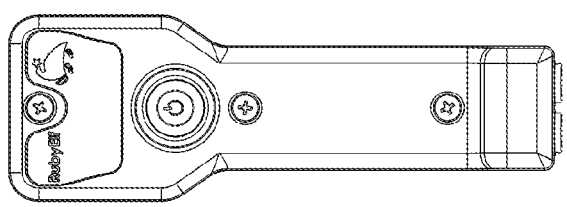
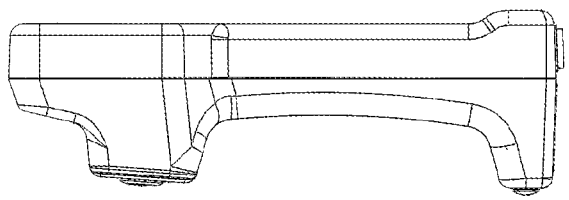
FIG. 12C　　　　　　　　　FIG. 12D

```
def prune_comp(comp, pulse_bin):
    PWTT_THRESHOLD = 0.15
    while True:
        comp.calc_pwtt()

# compare PWTT of composite to that of each pulse
        comp_pwtt_red = comp.pwtt['red']
        comp_pwtt_ir = comp.pwtt['ir']
        comp_pwtt_green = comp.pwtt['green']

red_pwtt_threshold = comp_pwtt_red * PWTT_THRESHOLD
        ir_pwtt_threshold = comp_pwtt_ir * PWTT_THRESHOLD
        green_pwtt_threshold = comp_pwtt_green * PWTT_THRESHOLD pruned_pulse = None
        for pulse in pulse_bin:
            red_exceeds_threshold = np.abs(pulse.pwtt['red'] - comp_pwtt_red) > red_pwtt_threshold
            ir_exceeds_threshold = np.abs(pulse.pwtt['ir'] - comp_pwtt_ir) > ir_pwtt_threshold
            green_exceeds_threshold = np.abs(pulse.pwtt['green'] - comp_pwtt_green) > green_pwtt_threshold
            majority_exceeds_threshold = (red_exceeds_threshold and ir_exceeds_threshold or
                                          ir_exceeds_threshold and green_exceeds_threshold or
                                          red_exceeds_threshold and green_exceeds_threshold)
            if majority_exceeds_threshold:
                # prune this pulse and try again
                pruned_pulse = p
                break if not pruned_pulse:
            break
        else:
            pulse_bin.remove(pruned_pulse)
            comp.sub(pruned_pulse)

# nothing left, done for now
        if comp.count == 0:
            break
```

FIG. 25

SYSTEM AND METHOD OF ASSESSING INTRA-ARTERIAL FLUID VOLUME USING INTELLIGENT PULSE AVERAGING WITH INTEGRATED EKG AND PPG SENSORS

RELATED APPLICATIONS

The present application is a continuation of U.S. patent application Ser. No. 17/229,741, filed Apr. 13, 2021, entitled PULSE WAVE TRANSIT TIME (PWTT) MEASUREMENT SYSTEM USING INTEGRATED EKG AND PPG SENSORS, which claims priority to U.S. Provisional Patent Applications Ser. No. 63/009,470, entitled PULSE WAVE TRANSIT TIME (PWTT) MEASUREMENT SYSTEM USING INTEGRATED EKG AND PPG SENSORS, filed Apr. 14, 2020, and to U.S. Provisional Application Ser. No. 63/067,147, entitled, SYSTEM FOR IMPROVED MEASUREMENT OF OXYGEN SATURATION, NON-INVASIVE DETECTION OF VENOUS AND ARTERIAL PULSE WAVEFORMS, AS WELL AS DETECTION OF CARBOXYHEMOGLOBIN, HYPERTROPHIC CARDIOMYOPATHY AND OTHER CARDIAC CONDITIONS, filed Aug. 18, 2020, and to U.S. patent application Ser. No. 17/135,936, entitled SYSTEMS FOR SYNCHRONIZING DIFFERENT DEVICES TO A CARDIAC CYCLE AND FOR GENERATING PULSE WAVEFORMS FROM SYNCHRONIZED ECG AND PPG SYSTEMS, filed Dec. 28, 2020, the entire disclosures of which are incorporated herein by reference in their entireties for all purposes.

TECHNICAL FIELD OF THE INVENTION

The present system relates to cardiac sensing systems using combined electrocardiographic (EKG) and photoplethysmographic (PPG) sensing systems.

Brief Description of Clinical Problem

Optimal hydration only makes sense within the context of the cardiac function of the given patient. There are many aspects to this optimal functioning, much of which is detailed in Appendix A. Though a full description is beyond the scope of the background needed here, the essential problem is that it is often difficult to assess clinically when to opt for fluid administration. Two organ systems—the lungs and the kidneys—have differing requirements for optimal functioning. The lungs do not work well with extra fluid, and the kidneys do not work well when arterial flow drops. Additionally, the mortality consequences of acute kidney failure from inadequate supply exceed that of acute lung failure from excess fluid. Drastically simplifying the situation, the lungs must be kept "dry" while the kidneys are kept "wet", all while maintaining adequate intravascular fluid needed to keep the flow of nutrients to tissues and removal of wastes from tissues.

The cost of incorrect management is high. There are 2.5-6.5 million cases of acute in-hospital acute kidney injury (AKI) per year, with mortality rates up to 20% and approximately $7500 added per case of inpatient AKI. Mortality and costs are much higher for ICU cases. What percentage of these cases could be avoidable is uncertain, but the recent studies done with the new Cheetah Nicom® system made by Cheetah Medical of Newton Center, Massachusetts, suggest many are (mortality reductions were not reported, but return on investment to hospitals were over three dollars for every dollar spent on non-invasive monitoring). A handheld, inexpensive, easy to use, and point-of-care solution to assessing intra-arterial volume, and whether to give or remove fluid would provide a tremendous benefit to clinicians facing difficult fluid management situations.

At present, the world's health care community has battled a global pandemic of Covid-19 disease for more than one year, commencing approximately in January of 2020. Many hospital managers and medical practitioners have learned that the complex and expensive legacy medical equipment, to include EKG and echocardiography machines, of a typical ICU, while valuable during normal times, is not well suited to the rapid tempo of an overburdened hospital ICU during a pandemic. The high cost of that equipment limits availability when ubiquity is the order of the day, and complexity carries attendant burdens of painstaking and time-consuming cleaning regimens at a time when personnel are in short supply. In particular, Covid patients in advanced stages frequently exhibit tachycardia, which limits the diagnostic value of echocardiography.

As will be shown fully herein, the present system is not so impaired. In particular, the preferred embodiment presented herein provides clinically useful patient information, with added benefits of being comparatively low-cost, fast and simple to use, and easily cleaned between patient applications. Thus, it is well suited to the challenges of a pandemic treatment environment.

SUMMARY OF THE INVENTION

In preferred aspects, the present system assesses intra-arterial fluid volume with a preferred system, comprising: (a) a device positionable against a person's skin; (b) at least one PPG sensor mounted on the device for measuring the person's PPG signal at multiple wavelengths of light; (c) a plurality of electrodes for measuring the person's EKG signal; (d) a computer logic system for receiving and analyzing the PPG signal and the EKG signal, wherein the computer logic system further comprises: (i) a system for identifying cardiac cycles in the EKG signal; (ii) a system for segmenting the PPG signal into a series of PPG signal segments based upon features in the identified cardiac cycles, (iii) a system for sorting the PPG signal segments into a plurality of bins based upon durations of (a) prior R-to-R cardiac cycles and (b) prior-prior R-to-R cardiac cycles, (iv) a system for generating a composite signal for each of the plurality of bins, and (v) a system for measuring a person's relative hydration level by comparing the composite signals generated from bins on the basis of the prior R-to-R cardiac cycles against the composite signals generated from bins on the basis of the prior-prior R-to-R cardiac cycles.

In further preferred aspects, comparing the composite signals generated from bins on the basis of the prior R-to-R cardiac cycles against the composite signals generated from bins the basis of the prior-prior R-to-R cardiac cycles may be done by: plotting a first line representing left ventricular output with arterial pulse shape as a function of prior R-to-R, the first line being based upon values of the composite signals generated from prior R-to-R cardiac cycles, plotting a second line representing venous return with arterial hemoglobin oxygen saturation as a function of prior-prior R-to-R, the second line being based upon the composite signals generated from prior-prior R-to-R cardiac cycles, and then determining the intersection point of the first and second lines as a metric of a person's relative hydration level. In addition to simple line plotting, however, comparing the composite signals generated from bins on the basis of the prior R-to-R cardiac cycles against the composite signals generated from bins the basis of the prior-prior R-to-R cardiac cycles may be done by: calculating a first relationship representing left ventricular output with arterial pulse shape as a function of prior R-to-R, the first relationship being based upon values of the composite signals generated from prior R-to-R cardiac cycles, calculating a second relationship representing venous return with arterial hemoglobin oxygen saturation as a function of prior-prior R-to-R, the second relationship being based upon the composite signals generated from prior-prior R-to-R cardiac cycles, and then comparing the first and second relationships as a metric of a person's relative hydration level.

In preferred aspect, the present system measuring a person's hydration level by detecting changes in the shape of a composite signal measured at an infrared wavelength of light by correlating intra-arterial fluid volume to the area under the curve of the composite signal measured at an infrared wavelength of light.

In preferred aspects, the system for generating a composite signal for each bin comprises a system for summing or averaging the PPG signal segments in the bin, and the composite signal is used to generate a composite Signal Prime Over Signal (SPOS) being the derivative of the composite signal normalized by the composite signal itself.

In various preferred physical embodiments illustrated herein, the present system is a hand-held device with the at least one PPG sensor mounted thereon and a plurality of electrode wires extending therefrom or mounted thereon. Alternatively, the present system may be positioned within a strap or band disposed around the person's chest or limb with at least one PPG sensor and the plurality of electrodes are disposed within the strap or band. Alternatively, the present system may be disposed in a patch with the at least one PPG sensor and at least one of the plurality of electrodes positioned therein.

System also provided for data transmission. Further systems are provided for iteratively removing aberrant PPG signal segments from the calculation of the composite signal.

The present system provides information regarding the intra-arterial fluid status. Such knowledge allows clinicians to know when to give, or remove, fluid. At heart is the analysis shown in the system top-level flow diagram of FIG. 1 resulting in arterial oxygen saturation fraction dependency 101 and arterial shape dependency 102. Specifically, the line/relationship describing the relationship between arterial PPG pulse shape and prior pulse EKG RtoR duration, and the line/relationship describing the relationship between arterial hemoglobin oxygen saturation fraction and prior-prior pulse EKG RtoR duration are first determined. These two relationships allow for assessment of the cardiovascular status as in FIG. 2. FIG. 2 shows a system top-level flow diagram, resulting in positions located on a surrogate Frank-Starling curve, before and after a challenge of hydration (either IV fluids or mobilization of fluids from the lower extremities). Curve 203 moves left with the fluid challenge to curve 204, and curve 205 moves rightward to 206 as a result of the fluid challenge. The "X" at 201 notes the pre-challenge position on the graph of the intersection of curves 203 and 205. The "X" at 202 notes the post-challenge position on the graph of the intersection of curves 204 and 206. The key insight is that movement upward from point 201 to 202 as a result of a trial of hydration represents a beneficial response in intra-arterial volume to hydration.

As described herein, the present system uses combined electrocardiography (EKG) and photoplethysmography (PPG) signals. (PPG is also commonly referred to as oximetry and the two terms will be used interchangeably throughout this specification). The former senses voltage produced by heart muscle contraction, and the latter measures light absorbed by tissues. Measurement at different wavelengths allows determination of volume. Changes in PPG signals reflect changes in blood volume and measurement at different wavelengths allows determination of arterial oxygen saturation.

As will be shown, the present system permits different insight than is currently available using existing hand-held, portable PPG systems/devices. In the present system, the combination of EKG and PPG signals utilize Pulse Wave Transit Time (hereafter "PWTT"), PPG Signal Prime Over Signal (hereafter "SPOS") curves, and PPG signal segments. As understood herein, a PPG signal segment means a PPG signal of any length shorter than, equal to, or longer than a cardiac cycle.

PWTT is the period of time taken between a heartbeat as measured by the onset of the QRS complex and the time at which the blood from the aorta reaches an extremity or other body part, as determined by the negative spike generated in the SPOS curve, also described as the derivative of the LED signal divided by the signal. Use of the signal derivative to determine the change in a LED signal heralding the arrival of an arterial pulse has been described in U.S. Pat. No. 10,213,123, assigned to MocaCare Corporation of Palo Alto, California. However, the present novel use of the signal prime over signal (SPOS) allows for greater insight, as it normalizes each wavelength signal and thus allows for comparisons between different wavelength SPOS curves.

Improved arterial oxygen saturation estimation is then generated by the present system from an SPOS curve of a composite sum/average of similar pulses. Prior (n−1) EKG R-to-R duration using R-wave peaks are calculated, as are prior-prior (n−2) R-to-R duration, PWTT, and SPOS. These are all used by the system to determine similarity of oximetry pulses, with similar pulses summed/averaged to form composite pulses, then compare differing composite pulses to gain cardiovascular insight.

Reduced PWTT corresponds to greater pulse wave velocity, though the greater velocity does not indicate better pump function. This is because the aortic bulb acts as a "mechanical capacitor", allowing metered delivery of arterial pulse volume. However, having obtained the PWTT for any given monitoring point on the body, this metric remains relatively stable and changes only gradually barring a sudden change in cardiovascular state (e.g. sudden change in heart rhythm such as onset of atrial fibrillation with rapid ventricular response). PWTT therefore provides a means by which to ensure accurate further data collection and analysis. This allows more reliable extraction of additional information from the combination of signals, and removal/minimization of introduced noise.

Measurement of absorption of light (per Beer-Lambert law) has the form Measurement$(t)=Ke^{[-Cf(t)]}$, and the signal prime over signal (SPOS) of the measurement will be:

$$SPOS(t) = -C\left(\frac{df(t)}{dt}\right).$$

The LED signals in plethysmography have the form:

$$\text{Signal}=K^* e^{[-Arterial(t)^*\Sigma(\alpha^* Hb)_{arterial}]} * e^{[-Venous(t)^*\Sigma(\alpha^* Hb)_{venous}]} \quad (1)$$

$\Sigma(\alpha^* Hb)_{arterial}$ and $\Sigma(\alpha^* Hb)_{venous}$ describe the composition of the blood and generally change slowly. Therefore, these two terms are constants across time for the duration of our sampling. (These terms will be explained in greater detail below).

Further, in healthy individuals, the venous flow is considered a constant. Current oximetry measures assume this, and this assumption was used by the present inventors for this initial exploration. Given this assumption, the equation reduces to:

$$\text{Signal} = K_1 e^{[-Arterial(t) * \Sigma(\alpha * Hb)_{arterial}]} \quad (2)$$

Using properties of the exponential function, and of its derivative, we derive the SPOS for the PPG Signal at several wavelengths (e.g., IR and Red).

$$SPOS(t) = -\left(\frac{dArterial(t)}{dt}\right) * \sum (\alpha * Hb)_{arterial} \quad (3)$$

Using the fact that the conceptual function Arterial(t) is the same for both Red and IR PPG Signals, we show that the SPOS of the signal from the IR LED ($SPOS_{IR}$) is directly proportional to the SPOS of the signal from the Red LED ($SPOS_{Red}$):

$$SPOS_{Red} = R * SPOS_{IR} \text{ or } SPOS_{Red}/SPOS_{IR} = R \quad (4)$$

Returning to the expression $$\sum \left(\alpha_{\mu Hb_x} * Hb_x\right)$$

This describes now different wavelengths of light are absorbed by the blood depending on the relative quantity of the types of hemoglobin present within.
Where:

$\alpha_{\mu Hb_x}$ = absorption coefficient for type of hemoglobin (deoxyhemoglobin, oxyhemoglobin, carboxyhemoglobin, methemoglobin), x, for the wavelength, μ.

$Hb_x$=fractional composition of blood of various types of hemoglobin. The Sum of fractional components of different types of hemoglobin=1.0

In the conditions of low levels of carboxyhemoglobin and methemoglobin (e.g. excepting situations such as carbon monoxide or cyanide poisoning), and using accepted standard absorption coefficients for $\alpha_{IR_{Hb}}$, $\alpha_{Red_{Hb}}$, $Hb = 1 - Hb_{O_2}$.

This results with the equation:

$$\left(\alpha_{Red_{HbO_2}} * Hb_{O_2}\right) + \left(\alpha_{Red_{Hb}} * (1 - Hb_{O_2})\right) = \quad (5)$$
$$R * \left[\left(\alpha_{IR_{HbO_2}} * Hb_{O_2}\right) + \left(\alpha_{IR_{Hb}} * (1 - Hb_{O_2})\right)\right]$$

The only unknown is $Hb_{O_2}$. Solving for $Hb_{O_2}$ gives us the fraction of the blood that is oxygenated (Arterial oxygenated hemoglobin Fraction, or Arterial Frac O2):

$$\text{Arterial Frac } O_2 = \frac{(-\alpha_{IRHb} * R + \alpha_{RedHb})}{R * (\alpha_{IRHbO_2} - \alpha_{IRHb}) + (\alpha_{RedHb} - \alpha_{RedHbO_2})} \quad (6)$$

This direct proportionality between SPOS for any wavelength and the summation of optical absorption coefficients times the fraction of hemoglobin is used extensively by the system.

Any recording of EKG, or oximetry signals, or their interaction, will have physiologic variability, as well as noise. Management of EKG noise have established protocols that have been built up over 100 years. Conditioning of oximetry signals do not have as long a history. Physiologic oximetry variability can occur from changes in venous flow (due to volitional movement, or passive movement from repositioning, or inflation/deflation of a blood pressure cuff/sphygmomanometer, etc.), respiration causing changes in intra-thoracic pressure with resultant change in blood volume return to the heart, or beat-to-beat duration variability. Noise, or non-physiologic variability, can also occur from a range of possibilities, from variation in the surface pressure and angle of application of the detector, to ambient light infection of signal collection, to DC drift of the detection circuit. Whatever the specific source of variation, without an intelligent approach to the signals, one cannot tell physiologic variability apart from non-physiologic variability (introduced noise).

Traditional means for dealing with noise introduced into oximetry signals is to filter. For example, a commonly used algorithm for detecting signal to noise ratio utilizes power within the frequencies below 20 Hz compared with power above this frequency (as described in MaximIntegrated AppNote AN6410.pdf provided by Maxim Integrated Corporation of San Jose, California). This frequency filtering highlights the underlying primary rhythm (heart rate) and smooths the appearance of the displayed waveform. However, pulses are not all the same, and treating them as if they are deletes valuable information that can be mined for deeper insight.

An alternative means by which to minimize variability is to average the oximetry over many pulses, as described in U.S. Pat. No. 10,485,433, assigned to Intel Corporation. This approach allows for minimization of introduced noise, but eliminates any information that could be gleaned from physiologic variability. This approach produces a single, homogenized, and representative pulse at the end of the process. However, pulses are not all the same, and treating them as if they are effectively obliterates some of the available information.

BRIEF DESCRIPTION OF THE DRAWINGS

FIG. 10 also shows the nomenclature and data structures used in the description of the present system.

FIGS. 12A to 12D show various views of a hand-held embodiment of the present system, having PPG and EKG sensors mounted thereon or attached thereto.

FIG. 25 is an exemplary algorithm for preparing Pulse Data Sets in accordance with the present system.

SUMMARY OF THE CARDIAC PHYSIOLOGY GERMANE TO THE INVENTION

Figure 3:
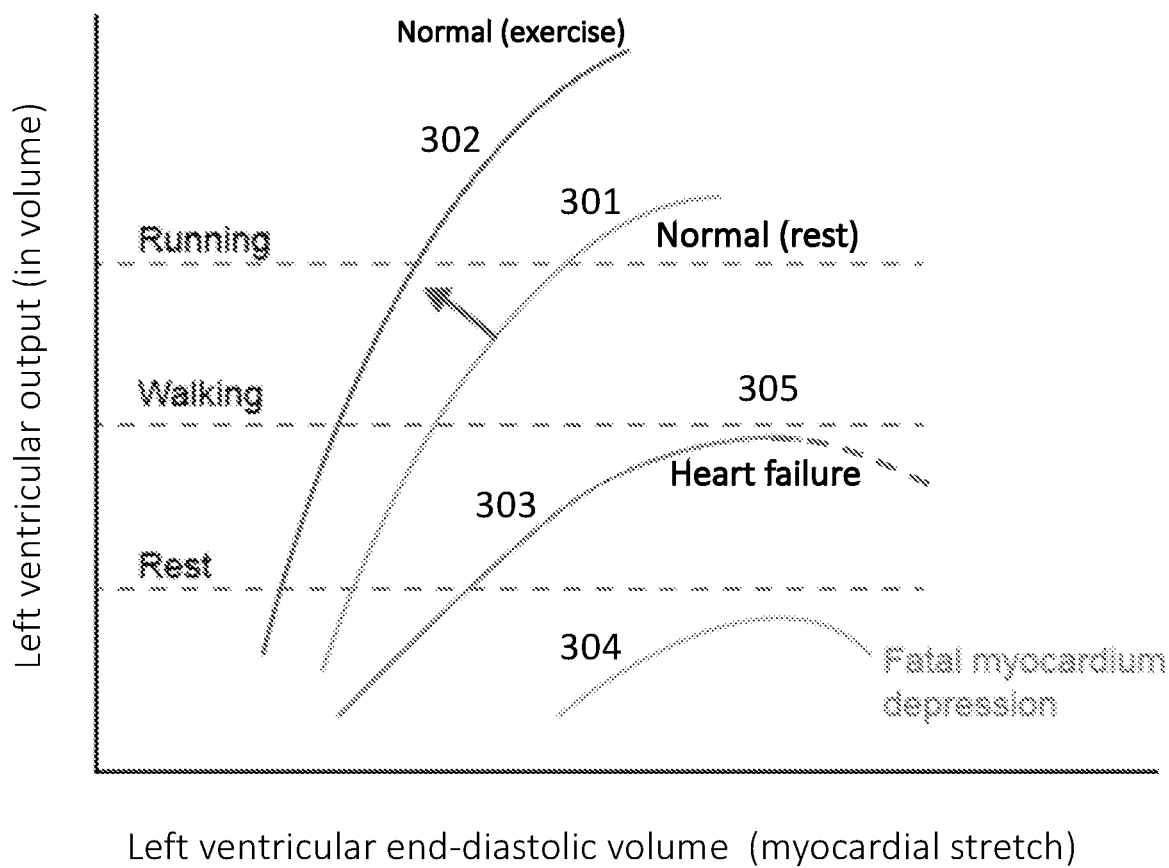
FIG. 3 is an illustration of the Frank-Starling relationship.

The Frank-Starling relationship in FIG. 3 (and Appendix A) shows that different conditions at end-diastole (the end of ventricular filling) result in different outcomes. Many elements, including intravascular fluid volume, contribute to the left ventricular end-diastolic volume; yet important factors are (1) the available intravascular volume, and (2) the time allowed for filling in the cardiac cycle, specifically the time between the end of one ventricular contraction and the onset of the next contraction is the time available for filling.

A number of curves are seen in FIG. 3. Some change in the state of the heart (and thus the applicable curve) is possible within a given individual, as seen between the two left-most curves 301 and 302. The "normal" resting curve of 301 moves left and upward to curve 302 in exercise, a normal healthy response. However, in most cases and at rest, the stretch-to-output curve describing the heart (also described as the "myocardial contractility") is relatively stable, barring a sudden change in the heart muscle (as with a heart attack). With heart failure (curve 303), the left ventricular output at any degree of left ventricular filling is less than with normal myocardial contractility at rest (301). Severe myocardial depression (304) is not compatible with life: a patient with such a heart condition will have symptoms of fluid build-up in the lungs even at rest. Note also that with heart failure curves there is a peak (305) to the left ventricular output, beyond which further ventricular filling yields ever worse output.

If the ventricle is thickened or otherwise less stretchy than normal, less stretch and thus less volume will be seen at the end of diastole. Still, for any limited range of time factors such as the pliability of the ventricle and the overall vascular volume are relatively fixed and can be treated as constant. It is notable that an echocardiogram, which takes data over 30 to 45 minutes (depending on the difficulty of visualization) also treats all cardiac attributes as fixed, even as they may be varying over the course of data collection. A system that gathers the needed information over seconds to a few minutes is reporting on a much narrower time frame than an echocardiogram, and can thus report on changes within the time it would take to carry out an echocardiogram. As opposed to these other cardiac parameters, the time for ventricular filling is not fixed. Thus, similar pulses will have similar ventricular filling times. (Note: While it may be difficult to determine exactly the duration of end-systole to end-diastole, for any narrow window of time that period will be a relatively fixed fraction of the R-peak to R-peak duration determined from the EKG corresponding to the observed oximetry signal).

The better the filling of the ventricle, the better the volume delivery of the ventricular contraction, until such time that the ventricle is stretched beyond the peak of the Frank-Starling curve (the essence of congestive heart failure). For the left heart, this volume delivery corresponds to an area under the curve analysis of the composite infrared (IR) PPG signal (see FIG. 4).

Figure 4:
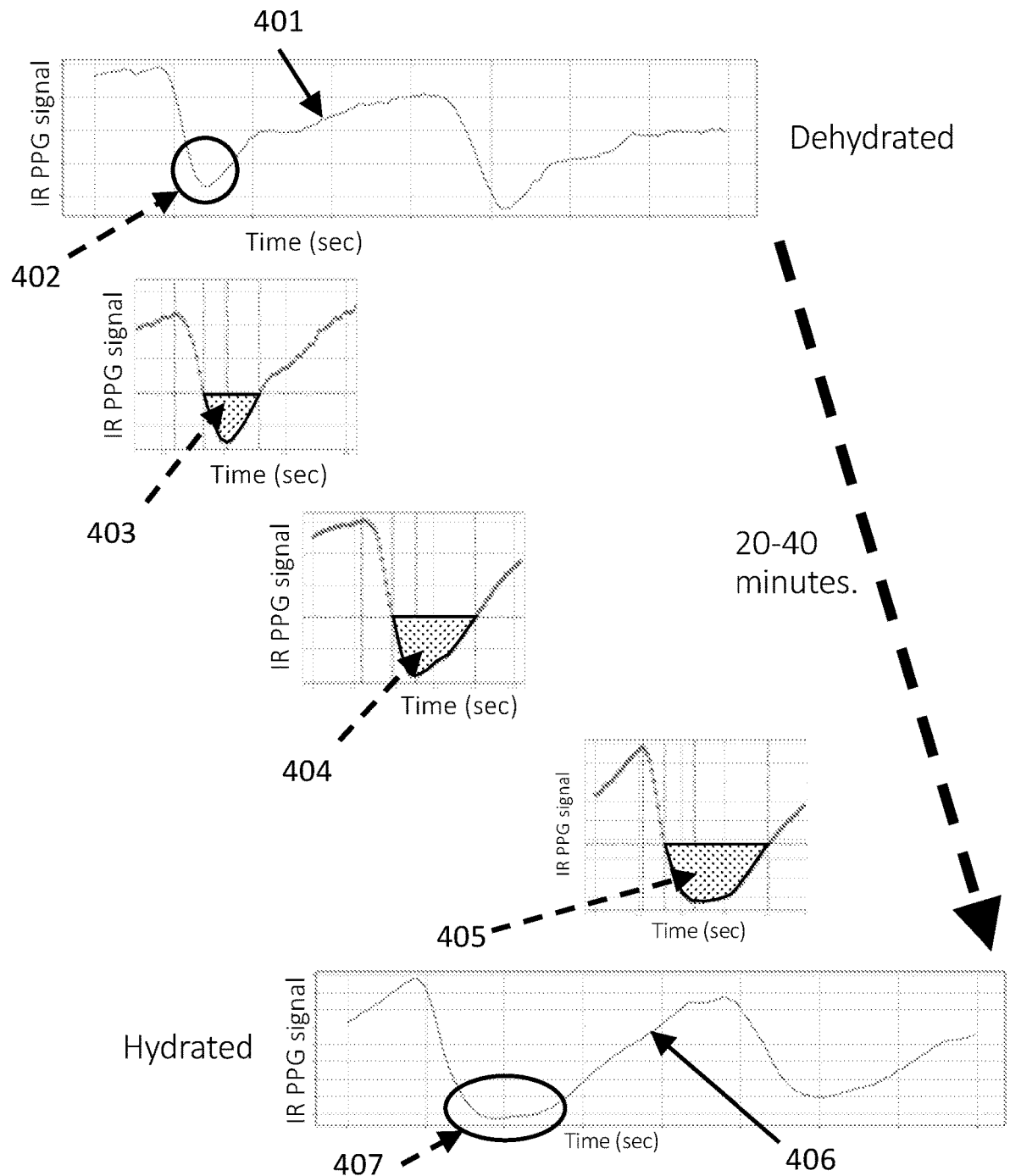
FIG. 4 is an under the curve analysis of a composite infrared (IR) PPG signal, showing changes to the curve under different patient hydration levels.

FIG. 4 shows how arterial volume change is reflected in the area under the IR PPG curve over the course of 20-40 minutes as fluid is absorbed from the small intestine after ingestion of oral fluids. Curve 401 shows the IR PPG signal in the dehydrated state. Region 402 shows the narrow valley (corresponding to the narrow arterial peak) that results from the heart's inability fully engage the "mechanical capacitor" of the aortic bulb due to lack of available intravascular fluid. Curve 406 shows the IR PPG signal in the post-rehydrated state and the widened valley 407 resulting from full engagement of the "mechanical capacitor" of the aortic bulb. Features 403, 404, and 405 show the enlarging quantified IR PPG signal area under the curve as fluid moves into the arterial space.

Figure 5:
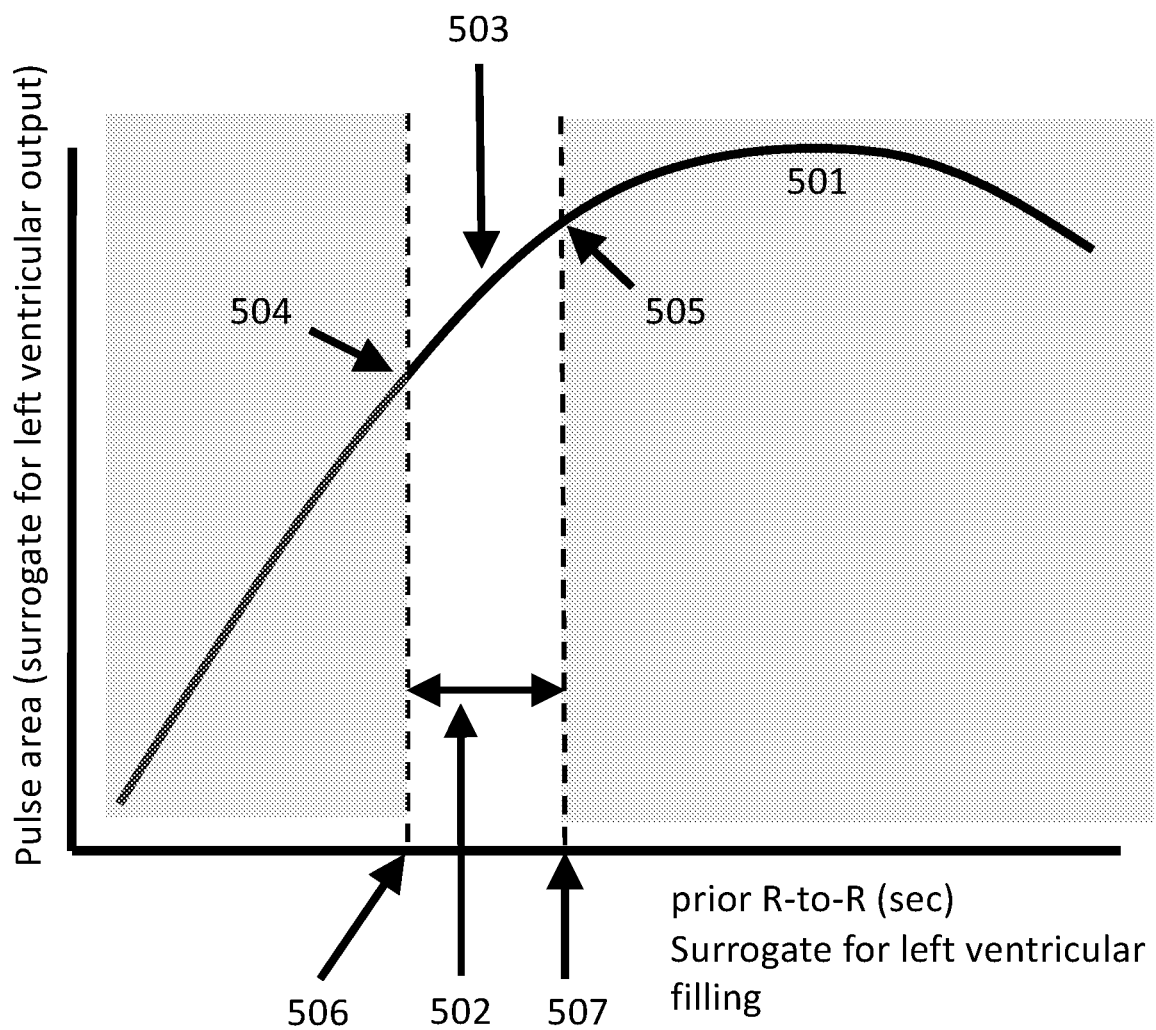
FIG. 5 is an illustration of "Pulse Area", showing an area under the curve value from a composite infrared (IR) PPG as a stand-in for the y-axis on the Frank-Starling curve.

Selection of similar pulses can then be done using oximetry pulses with similar prior (n−1) R-to-R duration which reflects the ventricular filling time. The pulses are grouped together, and ensuring the PWTT confirms this similarity, averaged, and an area under the curve analysis is done. This creates a surrogate Frank-Starling curve using prior (n−1) R-to-R duration a stand-in for the x-axis of the standard Frank-Starling curve, and an area under the curve value from a composite infrared (IR) PPG as a stand-in for the y-axis on the Frank-Starling curve, here labeled "Pulse area" (FIG. 5). Curve 501 is the surrogate Frank-Starling curve. The segment measured is 503, from point 504 to 505, by virtue of R-to-R variability from 506 to 507, yielding the sampling window 502.

Figure 6A:
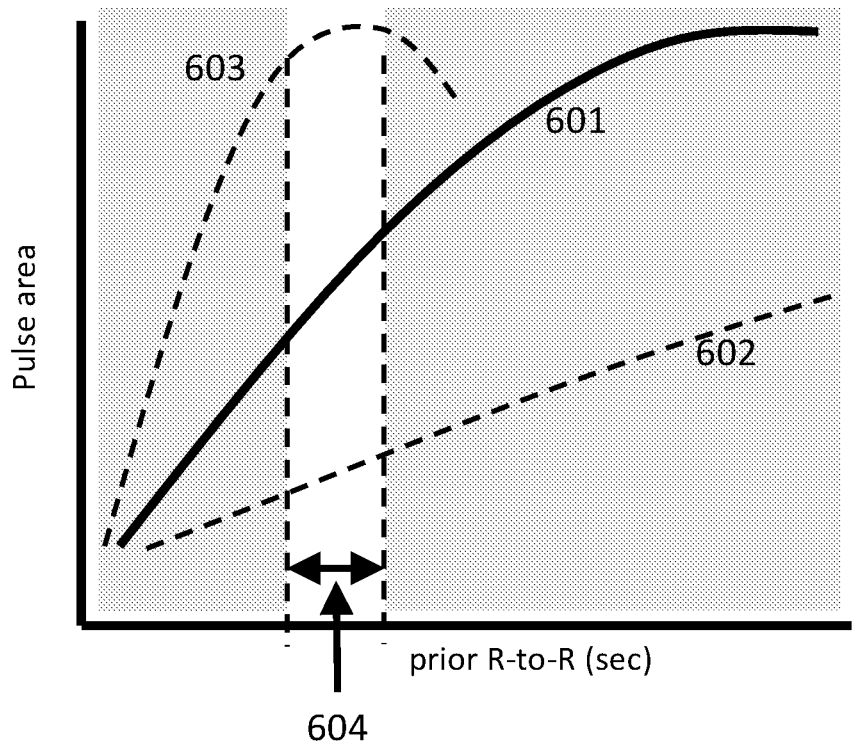
FIGS. 6A and 6B illustrate different Frank-Starling curves under different patient hydration conditions.
Figure 6B:
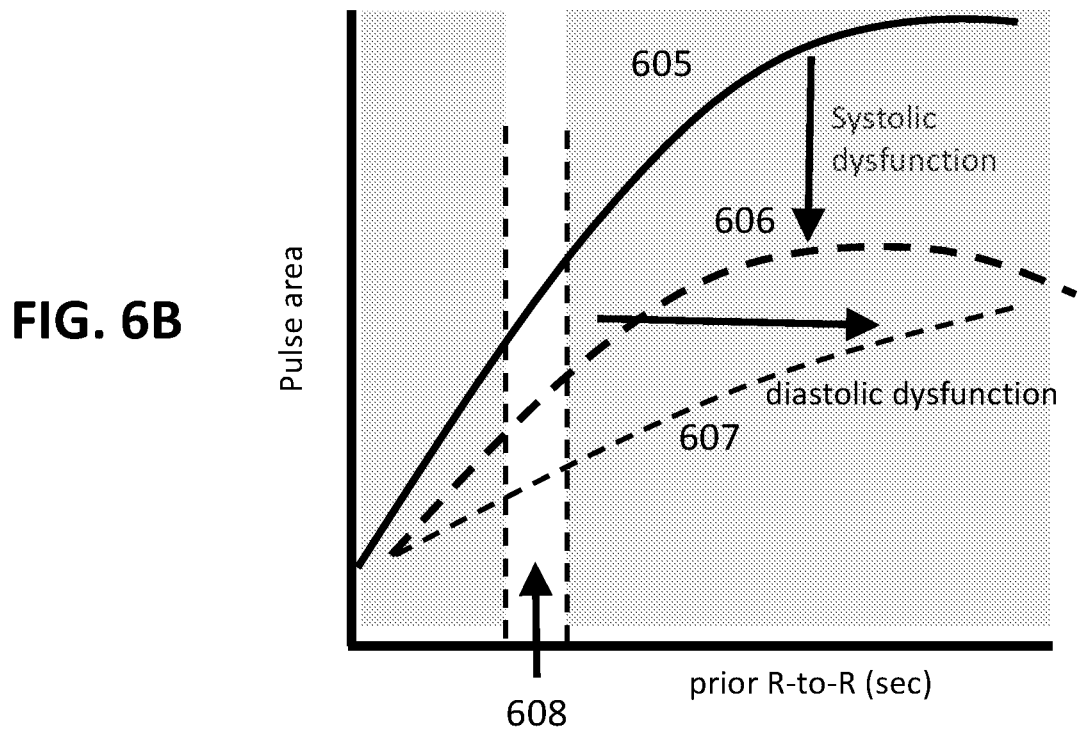

FIG. 6A and FIG. 6B show the dynamics of this surrogate Frank-Starling curve. FIG. 6A shows a surrogate Frank-Starling curve 601, and the changes seen in this curve with decreased intra-arterial fluid (602), and with increased intra-arterial fluid (603). Note that each of the curves 601, 602, and 603 are only sampled in the R-to-R window 604. Note also how curve 603 has been sampled at its peak. Further movement of this curve to the left will result in a falling Pulse area result. FIG. 6B shows the effect of decreased systolic (pump strength) function, as seen with interim heart attacks between sampling curve 605 and 606. FIG. 6B also shows the effect of stiffening of the heart (increased diastolic dysfunction). The curve 605 moves toward curve 607. This can be seen both transiently with increased blood pressure, and with thickening of the heart with chronic hypertension and also with hypertrophic cardiomyopathy. The stiffer the heart, the harder it is for the heart to relax and fill in diastole (relaxation), and thus the harder it is for the heart to take advantage of available fluid. As previously, the curves are sampled in the 608 window, as defined by the R-to-R variability.

The same dynamics of filling and contraction are at play with the right heart as with the left heart. Venous blood return to the right heart fills the right ventricle, and the more filling of the right ventricle in diastole (relaxation) in general the more the output of the right ventricle. However, with the right heart, (1) the better the filling and the better the contraction, the more blood is delivered through the lungs, which (2) is seen as improved systemic oxygenation (arterial oxygen saturation) two cycles later. This means that systemic arterial volume delivery will vary dependent on prior (n−1) R-to-R duration, and systemic arterial oxygenation will vary dependent on prior-prior (n−2) R-to-R duration. An additional caveat is that, whereas the venous volume return curve can be plotted with the Frank-Starling curve and normalized to equal height, the arterial oxygen saturation values for the surrogate venous return curves cannot be easily normalized against the volume delivery metric used for the surrogate Frank-Starling curve. Instead, the return volume is translated into arterial hemoglobin oxygen saturation fraction with a maximum value of 1.0 (100% saturation).

Figure 7:
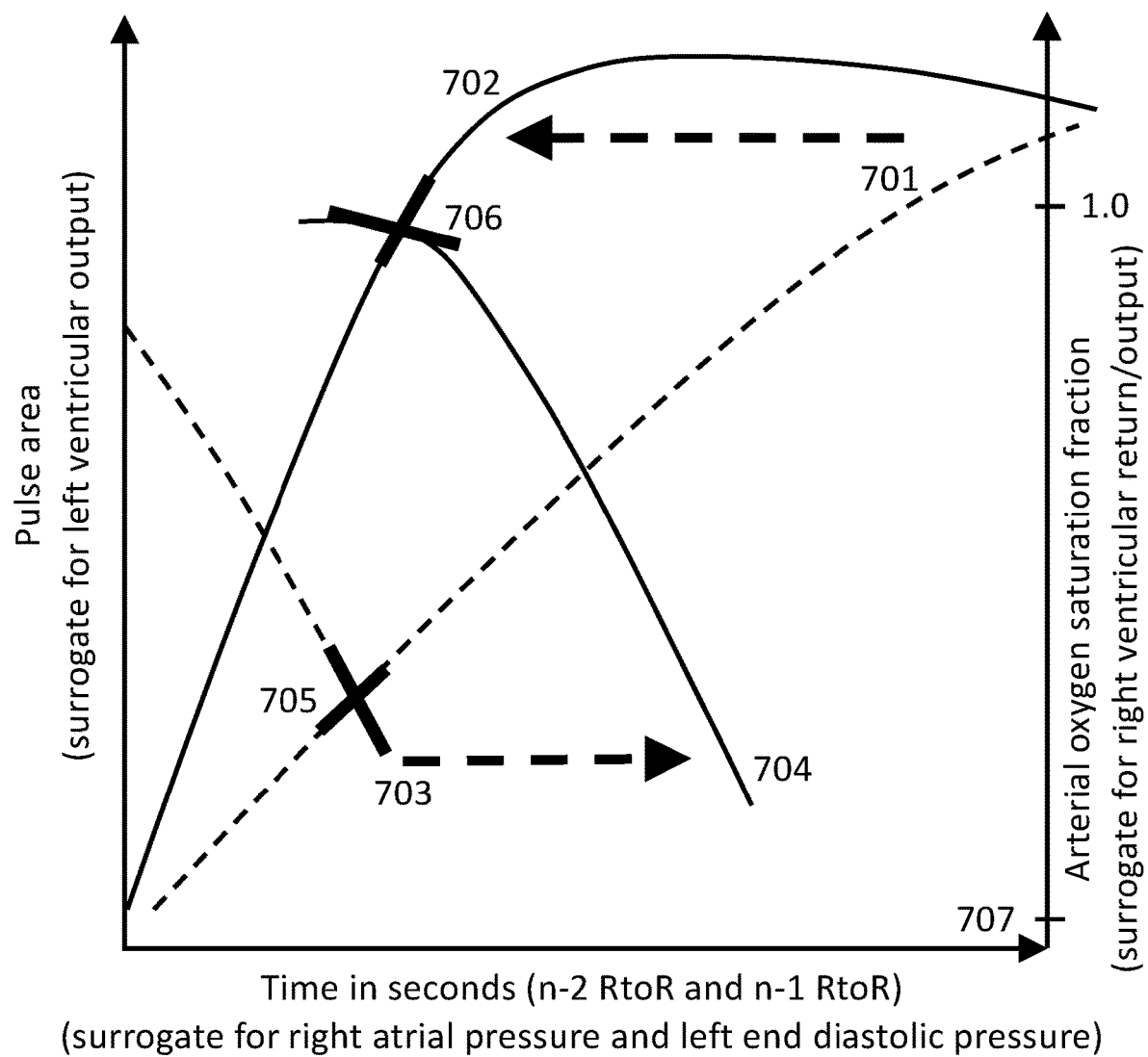
FIG. 7 shows the dynamics of the completed surrogate Frank-Starling curve including surrogate venous return.

FIG. 7 shows the dynamics of the completed surrogate Frank-Starling curve including surrogate venous return. As opposed to the adjusted left ventricular output curves that move left with increased intra-arterial fluid (curve 701, moving to 702), the adjusted venous return curves will move right with improved hydration (curve 703, moving to 704)—so long as left ventricular can respond to the increased fluid with increased output. Clinical position 703 therefore translates up to clinical position 706, corresponding to a beneficial response to fluid. Note that the upper end of the right y-axis is 1.0, while the lower end 707 is determined by the patient condition (a lower starting point expected with pre-existing heart or lung conditions).

With this understanding of the curves expected, extraction of similar pulses can be done on the basis of prior R-to-R or prior-prior R-to-R duration. PPG signals with similar prior (n−1) R-to-R duration are grouped together, and area under the curve analysis is done. PPG signals with similar prior-prior (n−2) R-to-R duration are also grouped together, and the oxygen saturation (arterial oxygen saturation) compared. In the clinical setting, the final picture yields clear movement in the operating state prior to a trial of intravenous fluid and after a trial of intravenous fluid, yielding needed data regarding the state of intra-arterial volume.

What is made possible is rapid, inexpensive, and point-of-care intra-arterial volume assessment, easily done at beside with minimal operator training.

DETAILED DESCRIPTION OF THE INVENTION

The central element of the present system is the identification and manipulation of PPG signals on the basis of prior R-to-R and prior-prior R-to-R duration. The present system then generates composite pulses from similar pulses.

In accordance with preferred aspects disclosed in U.S. Provisional patent application 62/955,196, entitled A System For Synchronizing Different Devices To A Cardiac Cycle, filed Dec. 30, 2019 and in U.S. patent application Ser. No. 17/135,936, entitled SYSTEMS FOR SYNCHRONIZING DIFFERENT DEVICES TO A CARDIAC CYCLE AND FOR GENERATING PULSE WAVEFORMS FROM SYNCHRONIZED ECG AND PPG SYSTEMS, filed Dec. 28, 2020, incorporated herein by reference in their entireties, the present system uses a specific trigger to set time=0 for each beat (e.g. EKG R-wave peak) and then stores each pulse from this start point until completing a full cycle of sensor data, such as with LED oximetry signals from maximum to minimum and back to maximum—which will be a waveform longer than a single pulse length. The next pulse waveform will have a t=0 at the next EKG R-wave peak, thus recording of the next beat will start before the recording of the last pulse waveform has completed. In absolute terms, the time corresponding to t=0 for the nth pulse will be referred to as time $t0_n$ throughout the rest of the specification.

Figure 8:
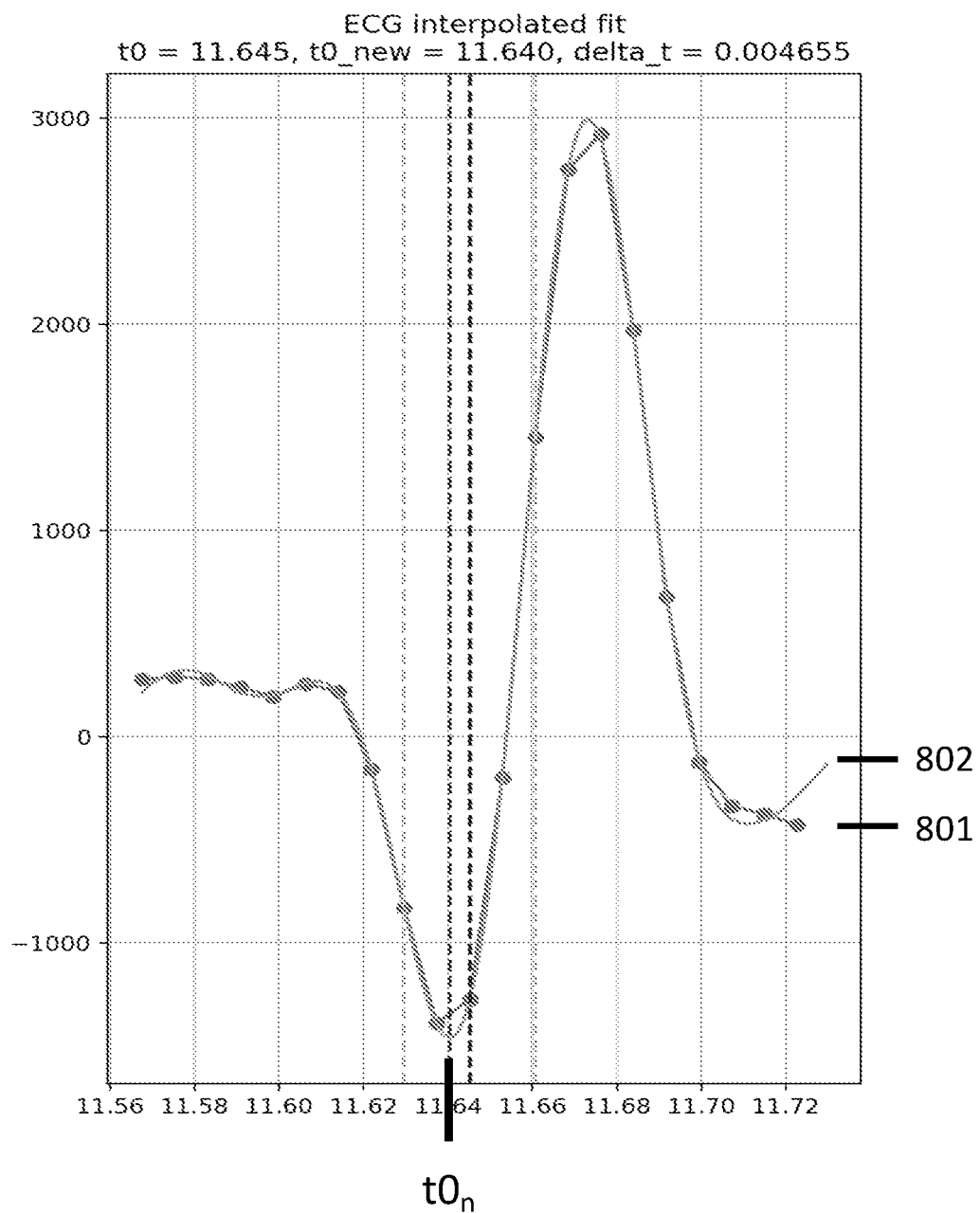
FIG. 8 shows the process of R-wave peak refinement used to generate tOn.

FIG. 8 shows the process of R-wave peak refinement used to generate $t0_n$. The example shows how the algorithm has determined the polarity of this collection to be negative (wires reversed), and thus the R-wave to be negative. The $t0_n$ of the R-wave peak is found using polynomial fitting (802) to EKG datapoints (801) and interpolation, then used to define a Pulse Data Set.

Figure 9:
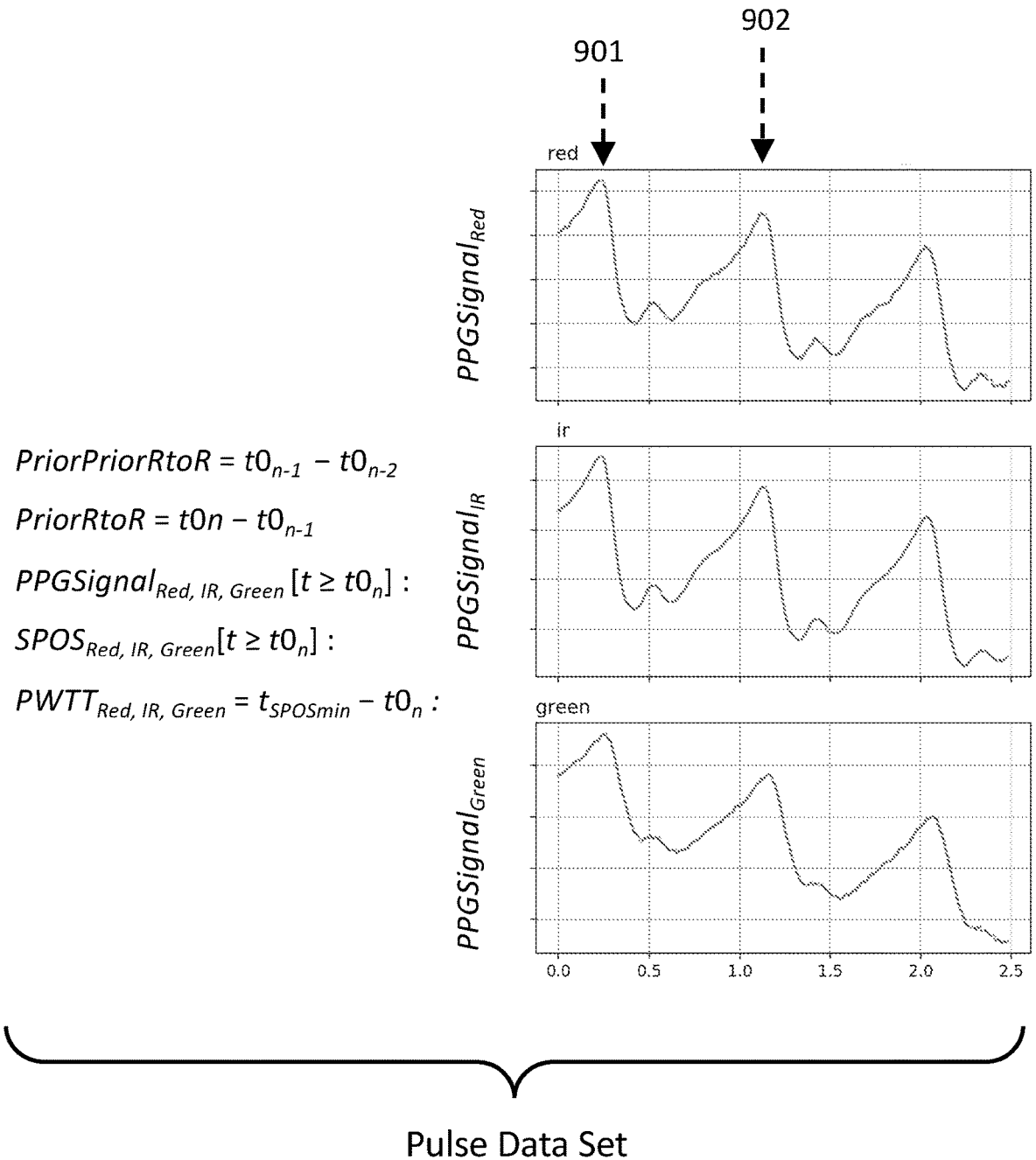
FIG. 9 shows the nomenclature and data structures used in the description of the present system.

FIG. 9 and FIG. 10 show the nomenclature and data structures used in the description of the present system. (Unless otherwise specified, PWTT=PWTTIR and PPG signal=PPG signalIR). The $t0_n$ time point is then used to define a Pulse Data Set with the PPG signals of multiple wavelengths (here red, infrared, and green). Stored with the PPG signal are the values for the prior R-to-R, and prior-prior R-to-R durations, the derived signals for Signal Prime over Signal (SPOS) for each wavelength, and the Pulse Wave Transit Time (PWTT) for each wavelength. Note the first PPG signal maxima (901) and the second PPG signal maxima (902). FIG. 10 shows the structure of the Composite Pulse Data Set, constructed from a group of Pulse Data Sets on the basis of a defined criteria (e.g. similar prior R-to-R, or prior-prior R-to-R duration). Note how the PPG waveforms are of duration longer than a single cardiac cycle, and are long enough to assure capture of both the first (1001) and second PPG signal maxima (1002).

Figure 11:
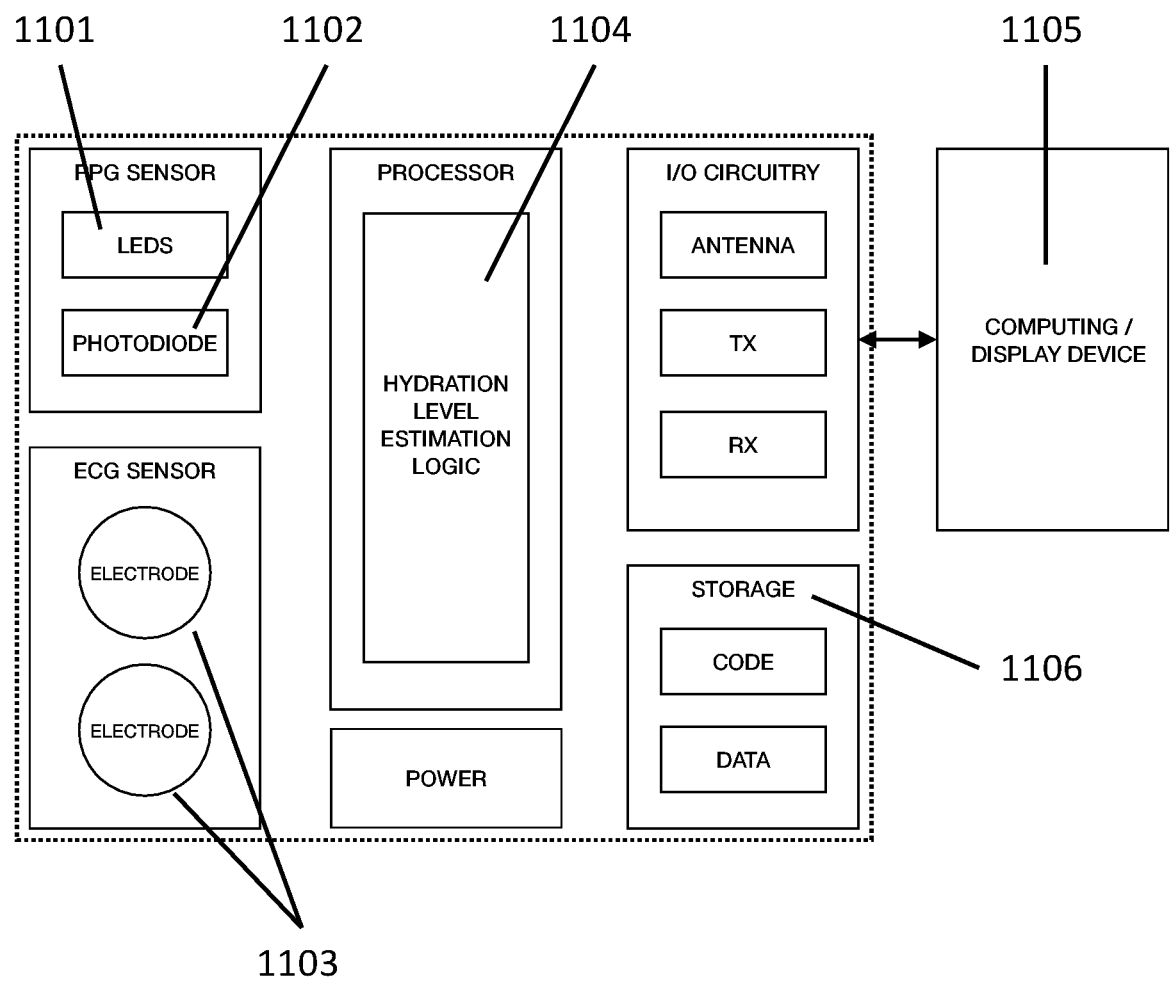
FIG. 11 is an exemplary illustration of various physical components of the present system.
Figure 13:
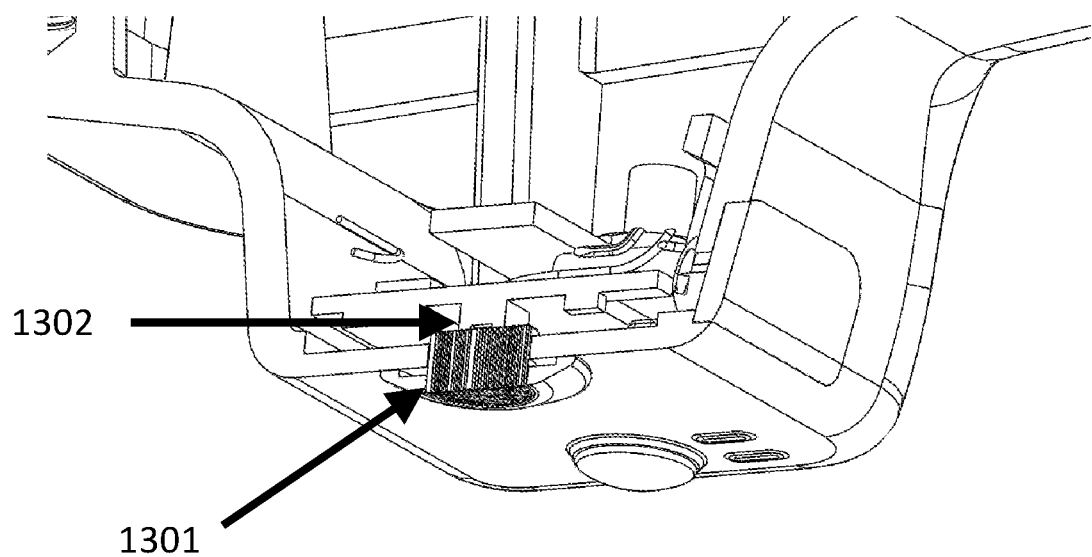
FIG. 13 is a cut-away view of a portion of the device of FIGS. 12A to 12D, showing an optical waveguide adjacent to a PPG sensor.

FIGS. 11-13 show a preferred device implementation of the system. The device block diagram shows the elements of the device/system, with multiple wavelength LEDs (1101) and a photodiode detector (1102), and EKG input from electrodes (1103) applied to the left and right chest (or left and right upper extremities. In preferred embodiments, signals are then fed to a processing unit (1104) carrying out "on-chip" logic that then generates Composite Pulse Data Sets from raw signal. The Composite Pulse Data Sets are then communicated via either wireless or direct cable connection to an "off-device" display/computing unit (1105) that provides the user with the final data in graphical form, and the recommendations with regard to fluid status. In preferred aspects, there is preferably also on-device storage (1106) for code as well as buffering and packetized transfer of data. In an alternate embodiment, the processing unit simply coordinates communication of raw ECG and PPG signal data to the external computing/display device which handles all aspects of the hydration level estimation logic. In yet another embodiment, all aspects of hydration level estimation are carried out by the processing unit, including rendering of graphics and making recommendations with regard to fluid status. In this case, the external computing/display device provides only the display function.

FIGS. 12A-D show various views of the PPG collection device. 1201 shows the optical waveguide (in front of LEDs and detector); 1202 shows optional incorporated EKG electrodes; 1203 shows plug-in connector sites for EKG lead wires to adhesive EKG electrodes (on right and left chest).

FIG. 13 shows detail of the PPG head, with an optical waveguide (1301) that abuts the LEDs and detector (1302) on the interior of the device. The optical waveguide allows for collection of PPG signals at sites other than the finger.

Figure 14A:
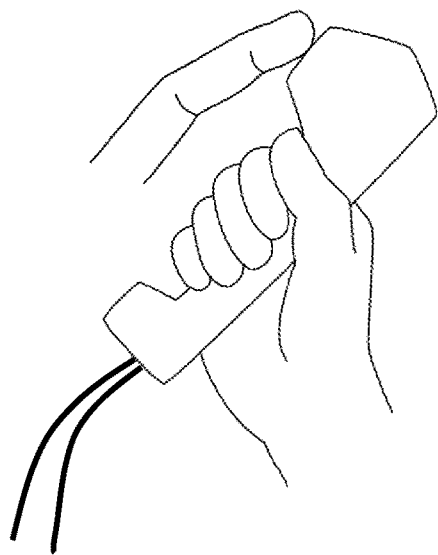
FIG. 14A is an illustration of the system of FIGS. 12A to 13 collecting PPG signals from a person's fingers.
Figure 14B:
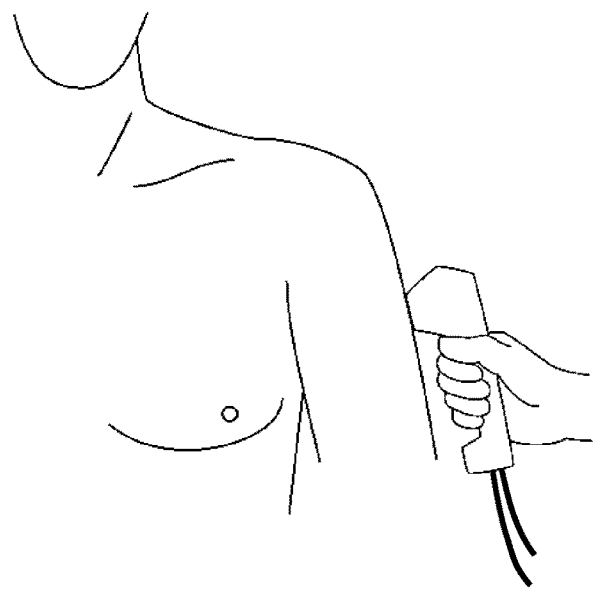
FIG. 14B is an illustration of the system of FIGS. 12A to 13 collecting PPG signals from the outside of a person's arm.

FIGS. 14A and 14B depicts the device in use collecting PPG signals from the finger (FIG. 14A), and the outside of the upper arm (FIG. 14B). The PPG measurement end of the device is applied to the skin in a stable fashion so that PPG measurement can be taken over the course of 1-2 minutes or more. EKG electrodes are applied to the left and right sides of the torso (or upper extremities) and connected to the plug-ins on the smaller end of the device.

Figure 15:
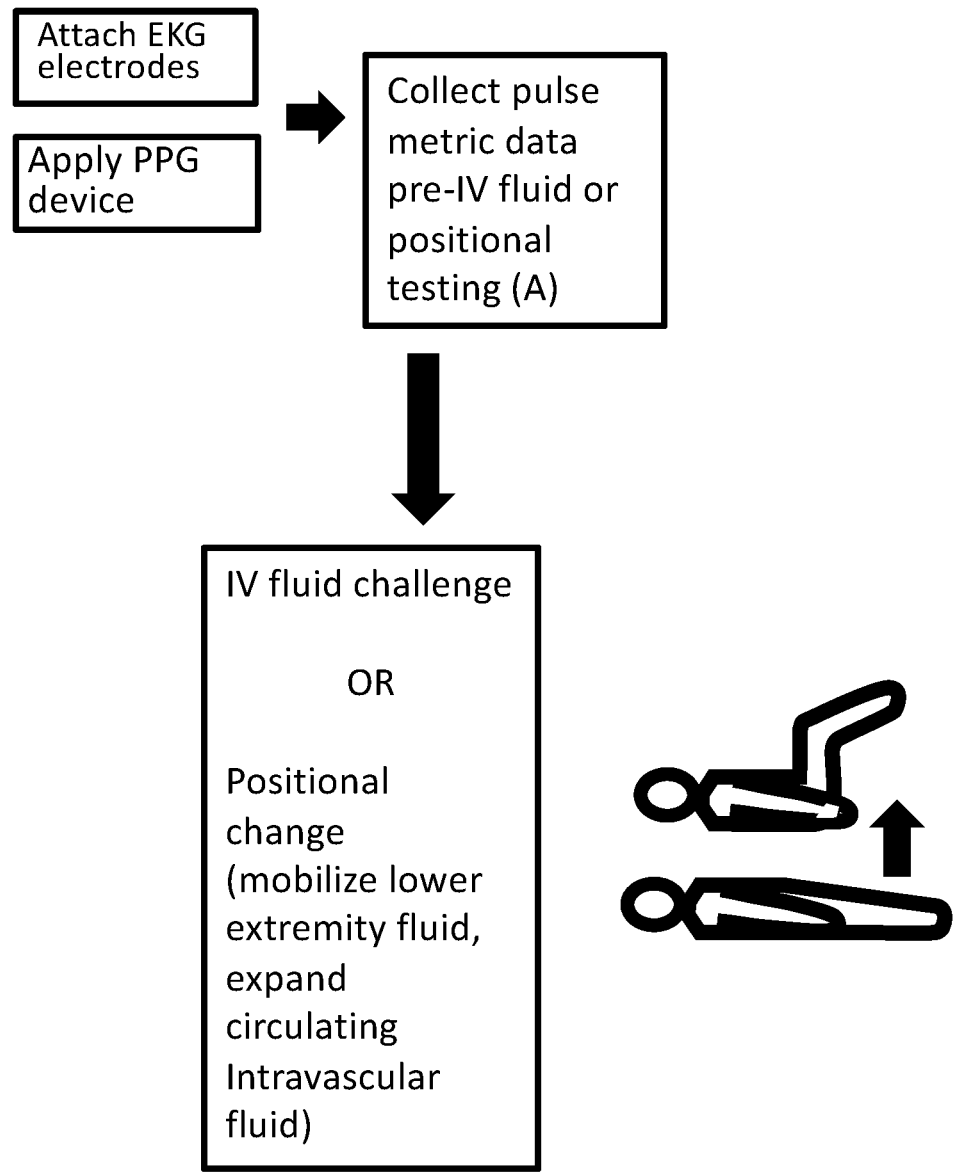
FIG. 15 is an illustration of a preferred method of use of the present system with a positional change of the patient acting as a fluid challenge.

FIG. 15 shows a preferred implementation of the system/device. EKG electrodes are applied on either side of the chest/torso (or on either upper extremity) and an extended PPG signal is collected. Analysis is then done to give a pre-hydration or positional change test. Administration of intravenous (IV) fluid is the more definitive means of injecting fluid into the venous system, yet requires time and trained personnel. Elevating the lower extremities above the level of the heart may mobilize a liter or more of venous blood and interstitial fluid, some immediately and some in a more delayed fashion. The venous blood and/or fluid mobilized by this method is less defined, but the technique is quick and easily done, and can provide the needed information by displacing a fairly large amount of intravascular fluid into the vena cava (and pre-loading/filling the right ventricle).

Figure 16:
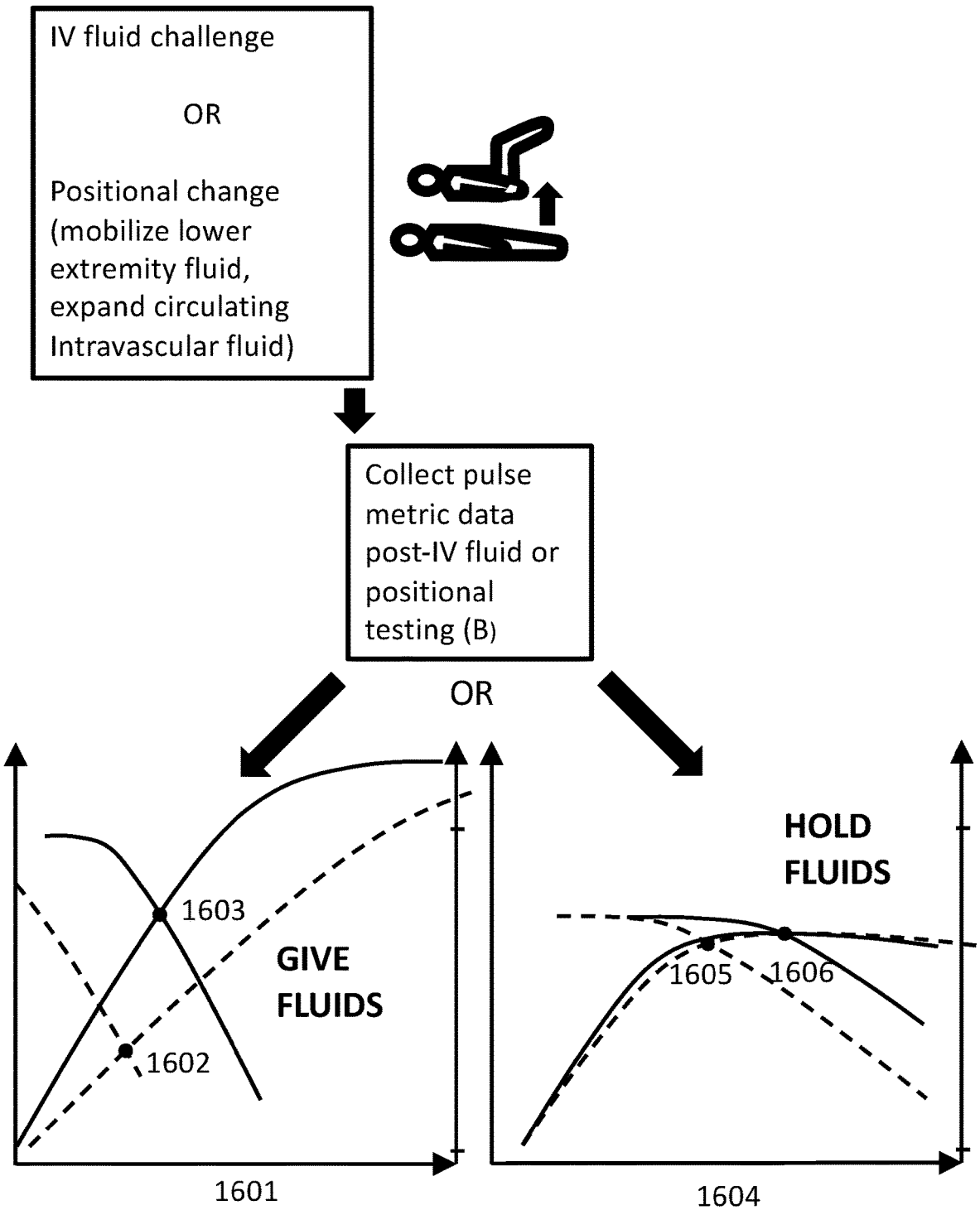
FIG. 16 corresponds to FIG. 15 after the fluid challenge.

The System/Device analysis is repeated as in FIG. 16 to give a post-hydration or positional change assessment. The change in operating point on the surrogate Frank-Starling curve (pre- to post-hydration) determines whether to give further fluid, hold fluid, or remove fluid.

Two different scenarios are shown: the curves of 1601, wherein the graphical position 1602 translates upward to position 1603, resulting in the recommendation to give more fluids. An alternative output is the graph of 1604, wherein the graphical position 1605 translates laterally but not upwards to 1606. This situation results in a recommendation to hold further fluids (and perhaps diurese/remove fluids). The present system then reveals how the cardiovascular system responded to the challenges. This provides the information needed to decide whether to hold further fluids, give fluids, or possibly give diuretics (forcing the kidneys to release sodium and water). The present system gives information regarding how far from peak intravascular status the patient is.

Figure 1:
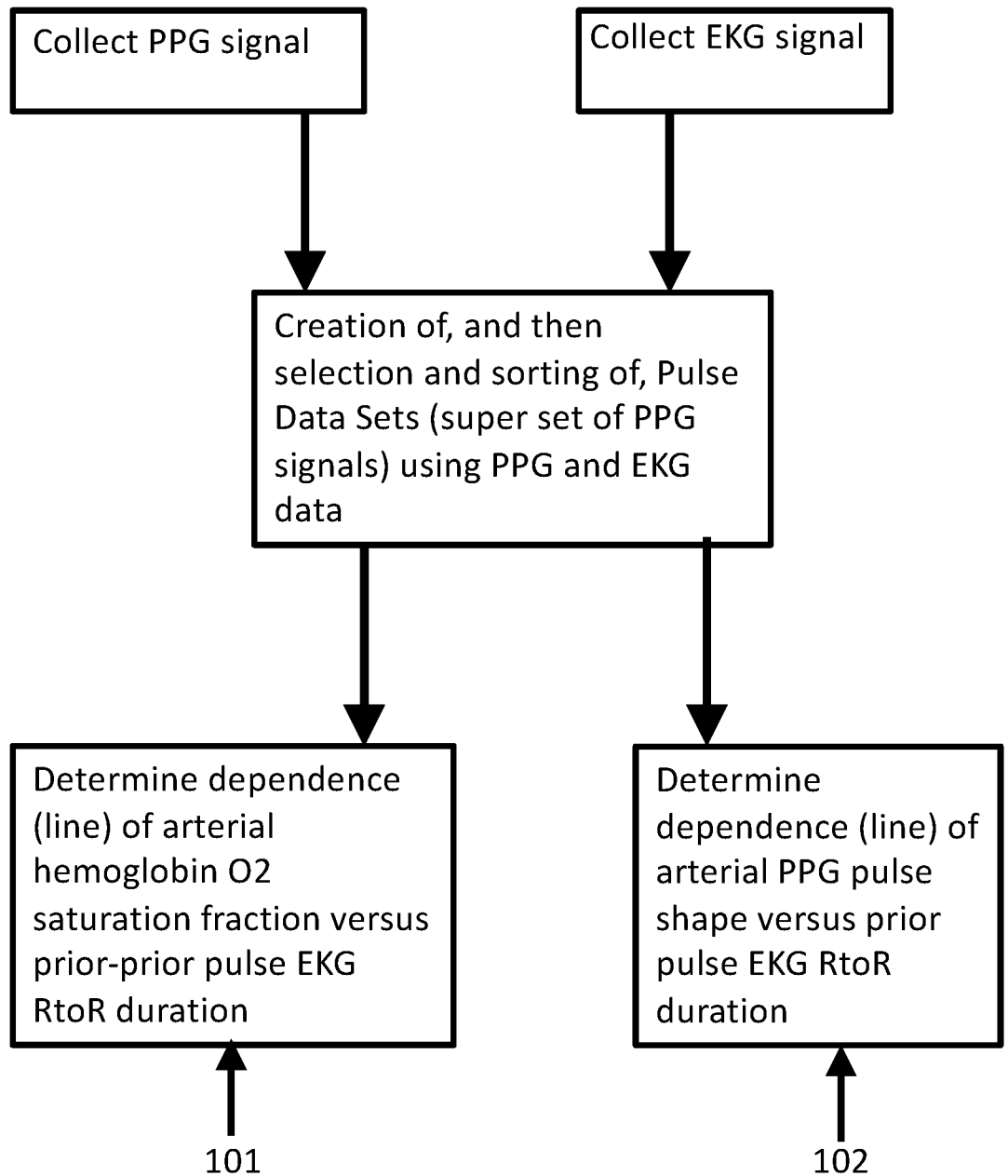
FIG. 1 is a top-level flow diagram of the operation of the present system.
Figure 2:
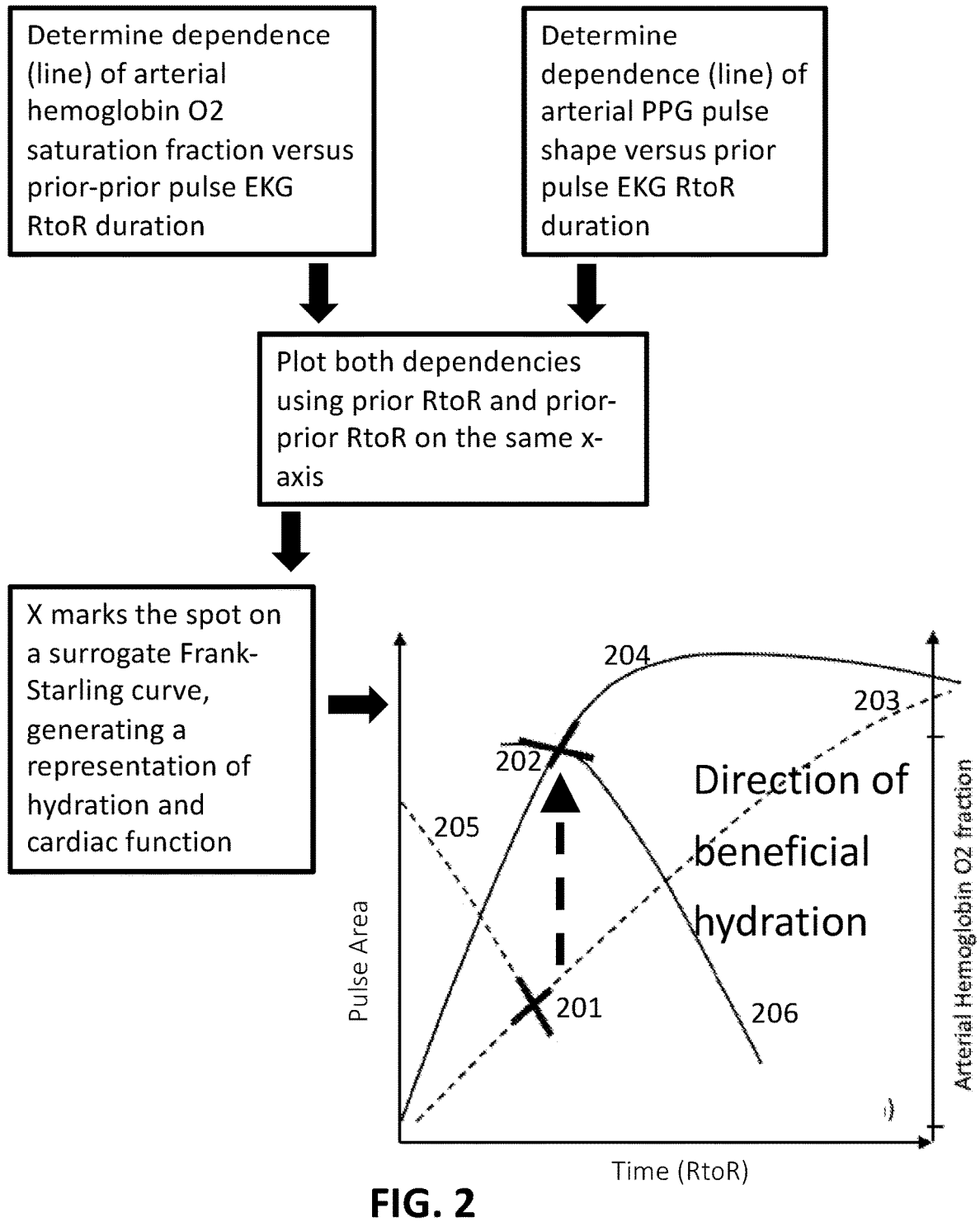
FIG. 2 is an assessment of cardiovascular status determined by the present system as presented on a surrogate Frank-Starling curve.

Returning to FIG. 1, PPG and EKG signals are collected. PPG waveform selection is performed to screen out aberrant beats considerably different than the majority of pulses, such as premature ventricular contraction beats, an example where the cardiac contraction does change appreciably from the beat prior.

Figure 17:
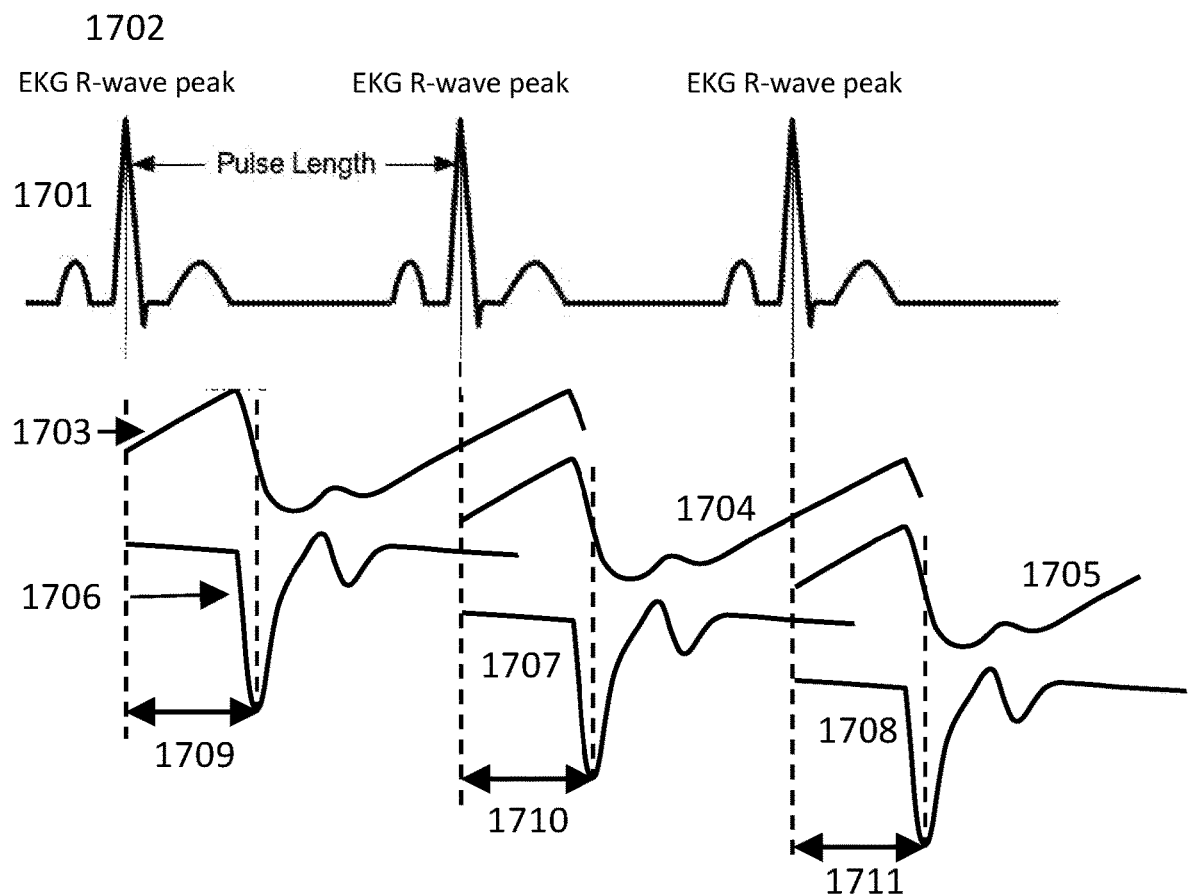
FIG. 17 is an illustration of EKG and PPG signals measured over time and generated SPOS signals corresponding thereto.
Figure 18B:
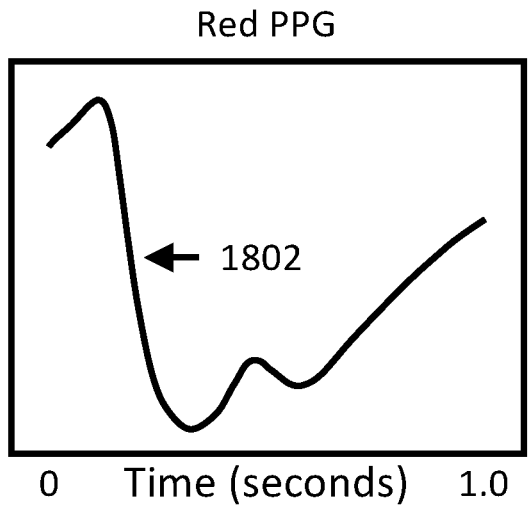
FIGS. 18B to 18D show PPG signals associated with this pulse at different wavelengths of light.
Figure 18A:
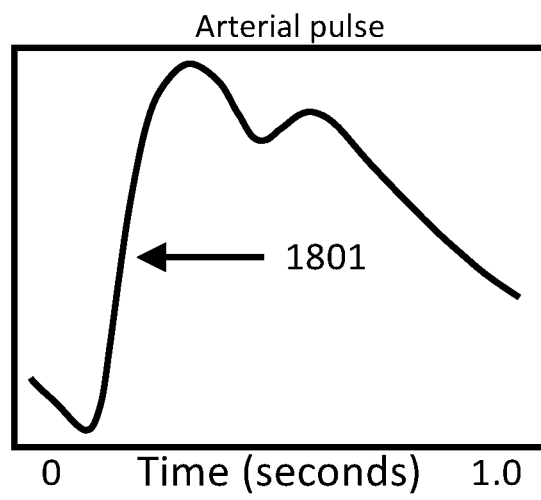
FIG. 18A shows a detailed plot of an arterial pulse.
Figure 18C:
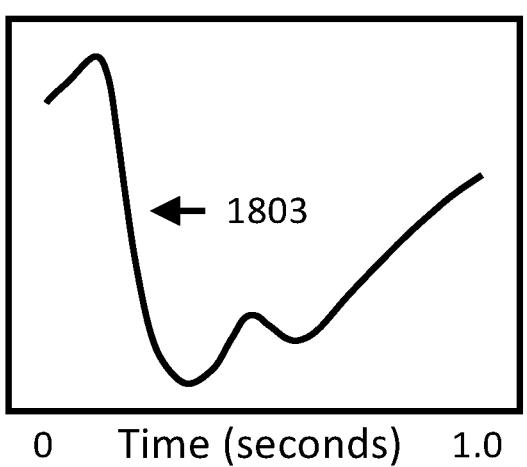
Figure 18D:
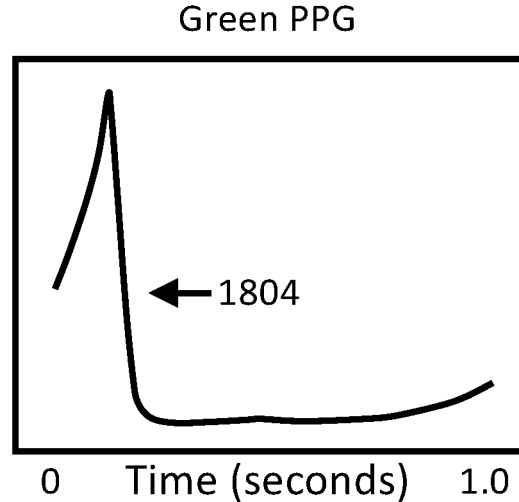

FIG. 17 shows: EKG signal (1701); EKG R-wave peak (1702); PPG signal segments (contained within Pulse Data Sets) (1703, 1704, 1705); SPOS signals (contained within Pulse Data Sets) (1706, 1707, 1708); PWTT using SPOS (also contained within Pulse Data Sets) (1709, 1710, 1711). This demonstrates selection of one of the PPG signals (in the current implementation red, infrared, and green are used, though the approach is not limited to using these alone) with full time length for both PPG signal and SPOS longer than the R-to-R duration.

The present method and system of intelligent pulse averaging counters the effect of drift in "K" (seen in equation 1), related to absorption from fixed elements in the tissue being analyzed. With averaging, some pulses will have an upward drift in K, some will have a downward drift, leaving the averaged pulse with more options for data point comparisons across the composite pulse width.

Figure 19A:
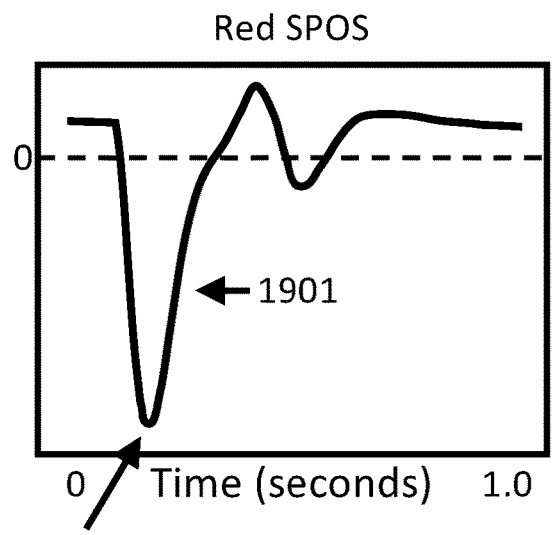
FIGS. 19A to 19C illustrates calculated SPOS curves corresponding to the PPG signals of FIGS. 18B to 18D.
Figure 19B:
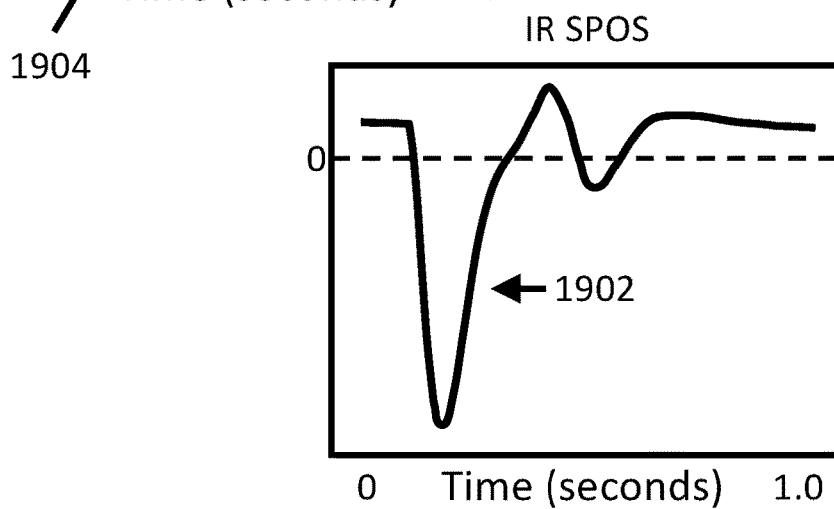
Figure 19C:
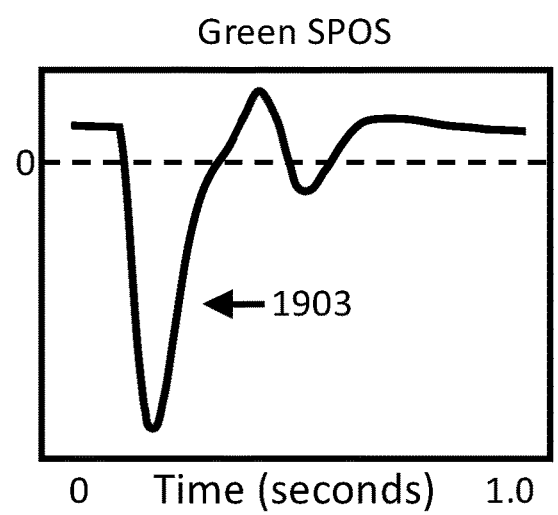

FIG. 18 shows more detailed plots of an arterial pulse (1801), and PPG signals associated with this pulse (Red 1802, IR 1803, Green 1804). FIG. 19 shows the SPOS of Red (FIG. 19A, curve 1901), infrared (IR) (FIG. 19B, curve 1902), and green (FIG. 19C, curve 1903), derived from PPG signals for the arterial waveform in FIG. 18A. Also noted in the characteristic "negative spike" of the SPOS waveform (1904).

FIG. 18-19 show how SPOS generates similar shaped curves for the LED signals for the different wavelengths, magnitude differing only by a multiplier that is the $\Sigma(\alpha*Hb)$ for the specific wavelength. In light of this, the present system includes the two novel approaches of examining the SPOS signal in the region of the "negative spike" to determine:

the linearity of the rising LED SPOS signal, or
the fit of the SPOS signal to a combination of Gaussian derivatives and/or exponential and/or polynomial equations.

Given the similar shapes for the SPOS curves, any such fitting can be applied to one wavelength to yield a fitted curve. Fitting to another wavelength only requires finding the magnitude needed to best fit that curve. For example, if f(t) best fits the infrared LED SPOS, then "A" needed to best fit A*f(t) to the SPOS for the red LED signal yields the arterial oxygen saturation just as with the equation 1. The difference with the standard formulation is that this fitting is based on many more time points (up to 50 at slower heart rates) than the two (maximum and minimum) used in the standard formulation.

Figure 20:
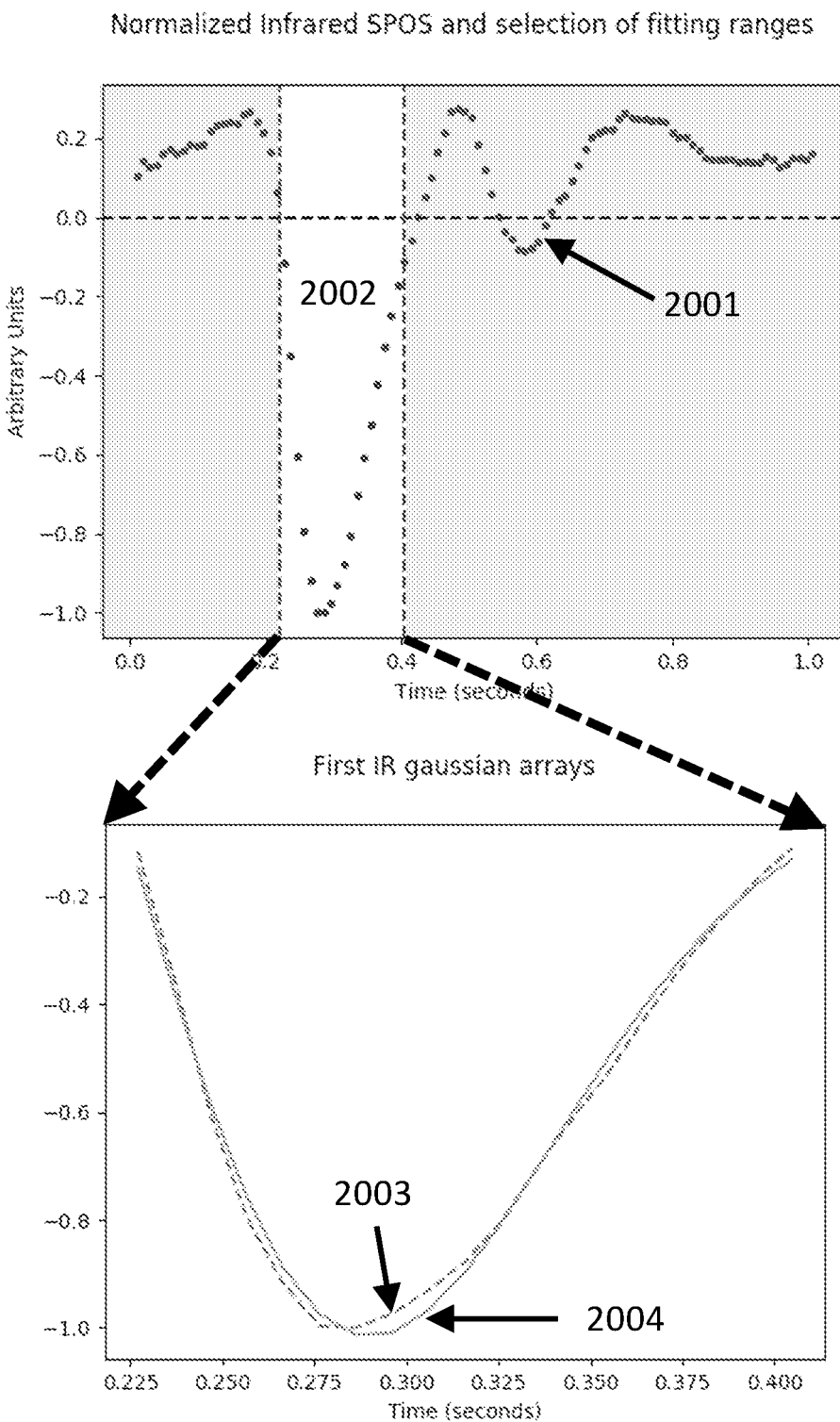
FIG. 20 is an illustration of one-sided Gaussian fitting.

FIG. 20 shows this concept using a one-sided Gaussian derivative fitting. Curve 2001 are the datapoints of a collected Composite IR SPOS signal with a fitting window 2002 selecting out the negative SPOS "spike". Curve 2003 shows the datapoints for the window in an expanded plot, also showing the one-sided Gaussian derivative fitted curve 2004.

The interval of the fitting window selected (the SPOS "negative spike"), or subset thereof (e.g. the rising SPOS right half of the "negative spike") represents a unique period wherein a single dominant and coherent physiologic event—the contraction of the left ventricle during the time of an open aortic valve—is clearly separate from other confounding physiologic features. This allows for extraction of parameters, which can then be applied to the entire PPG sensor pulse waveform.

Multi-Beat Complexes and Prior R-to-R and Prior-Prior R-to-R Dependencies

The next step with all analyses in the present system is to create multi-pulse dependencies. Multi-beat complexes consist of an EKG segment with a defined R-to-R duration, tied to PPG signals for a subsequent pulse. Currently the PPG signals consist of red, infrared, and green LED signals, though the approach is not limited to these wavelengths. One multi-beat relationship is between a set of PPG signals and the immediately prior R-to-R duration (n−1 R-to-R duration). The second multi-beat relationship is between the arterial oxygen saturation for a set of PPG signals and the prior-prior R-to-R duration (n−2 R-to-R duration). The advantage of this novel approach is that it categorizes PPG waveforms on the basis of similar ventricular filling.

The filling stage of the left heart ventricle in one cycle will correspond to the ventricular contraction or emptying stage in the next cardiac cycle. Stated another way, the pre-contraction left ventricular state will depend upon the time available to fill the left ventricle after that last contraction. Ventricular function will therefore vary slightly beat to beat depending on the variability of the pulse length. When measuring the arterial pulse, therefore, the shape of the PPG signal seen will be dependent on the R-to-R duration of the n−1 pulse (with the current PPG pulse taken as "n"). The knowledge of prior (n−1) R-to-R duration allows for selection of similar pulses. However, note that pulses selected by this method are only similar to the point of the shortest pulse selected, after which point the "rolloff" of the composite pulse being constructed is no longer valid. Because the composite pulse length is limited, arterial oxygen saturation can be derived for this composite pulse, though no trend attributable to right heart variability can be assessed.

If the analysis is of arterial oxygen saturation related to R-to-R duration, the more important relationship is between arterial oxygen saturation for a given pulse PPG signal (pulse "n") to the prior-prior R-to-R duration (also denoted as the n−2 R-to-R). Because the pulse transits through the lungs prior to reaching the left heart, the results of the ventricular filling of the right heart will be seen in the arterial system one cardiac cycle behind the effect of ventricular filling of the left heart.

Prior R-to-R Dependency

Figure 21:
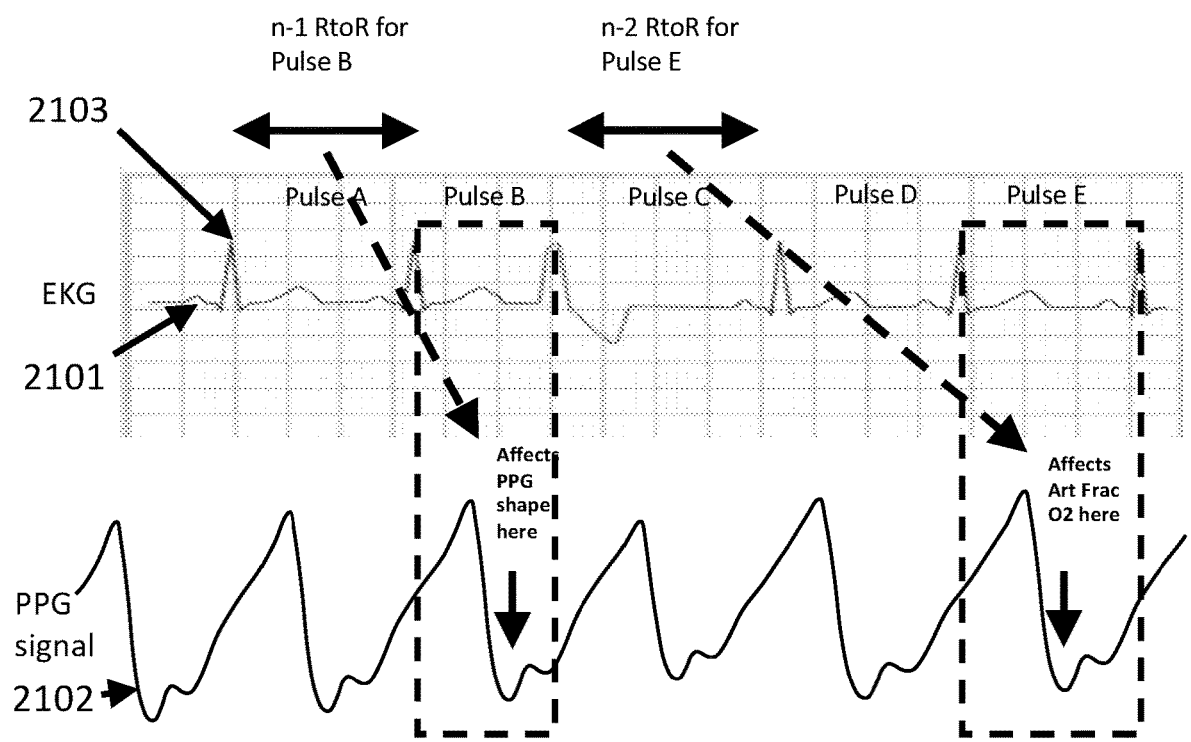
FIG. 21 illustrates a time-correlated comparison of EKG and PPG signals showing the relationships in creation of multi-beat dependencies, which are then used to create composite waves.

FIG. 21 depicts a time-correlated above/below comparison of EKG (curve 2101) and PPG signals (curve 2102) showing the relationships in creation of multi-beat dependencies, which are then used to create composite waves. An EKG signal is taken over five pulses/cardiac cycles (labelled pulses A, B, C, D, and E). As seen, the pulses are of different duration, reflecting the reality that heart rate varies slightly over time (with the exception of certain cases of pacing with an implanted pacemaker). The current system places PPG signals in different "bins" based on R-wave peak (2103) to R-wave peak (R-to-R) durations, with pulses in the bins being analyzed together so as to generate a composite wave representative of the bin.

In one implementation three bins are used, based on short R-to-R duration, intermediate R-to-R duration, and long R-to-R duration—though it is understood that the present invention is not limited to only three categories. It is also understood that the approach here is not limited to the use of red, green, and infrared signals used here, but may encompass any number of wavelengths of light as the particular situation dictates.

In the first dependency, and referring to FIG. 21, the pulses are sorted into categories based on the length of the previously measured pulse (and not the length of the current pulse for which the PPG signal is being measured). In this first sorting, FIG. 21 pulses B and E are categorized on the basis of their immediately prior pulse ("n−1") R-to-R duration (i.e.: R-to-R duration of pulses A and pulse D). Since pulses A and D are of intermediate duration (pulse B is a short pulse and pulse C is a longer pulse), the PPG signal of pulse B in the 2-beat dependency A-B and the PPG signal of pulse E in the 2-beat dependency D-E are therefore both placed in the intermediate (corresponding to n−1 R-to-R) bin. This is the case even though pulses B and E have considerably different PPG signal lengths.

Also seen in FIG. 21 is selection based on another dependency, that of PPG signal arterial oxygen saturation with prior-prior R-to-R duration (prior-prior R-to-R duration is also denoted as the n−2 R-to-R). In this implementation, the PPG signal of pulses A and C are grouped together. The oxygen saturation of pulse C is related back to the R-to-R duration of pulse A. The arterial oxygen saturation of pulse F (off FIG. 21 to the right) will have dependency on the R-to-R duration of pulse D.

Figure 22:
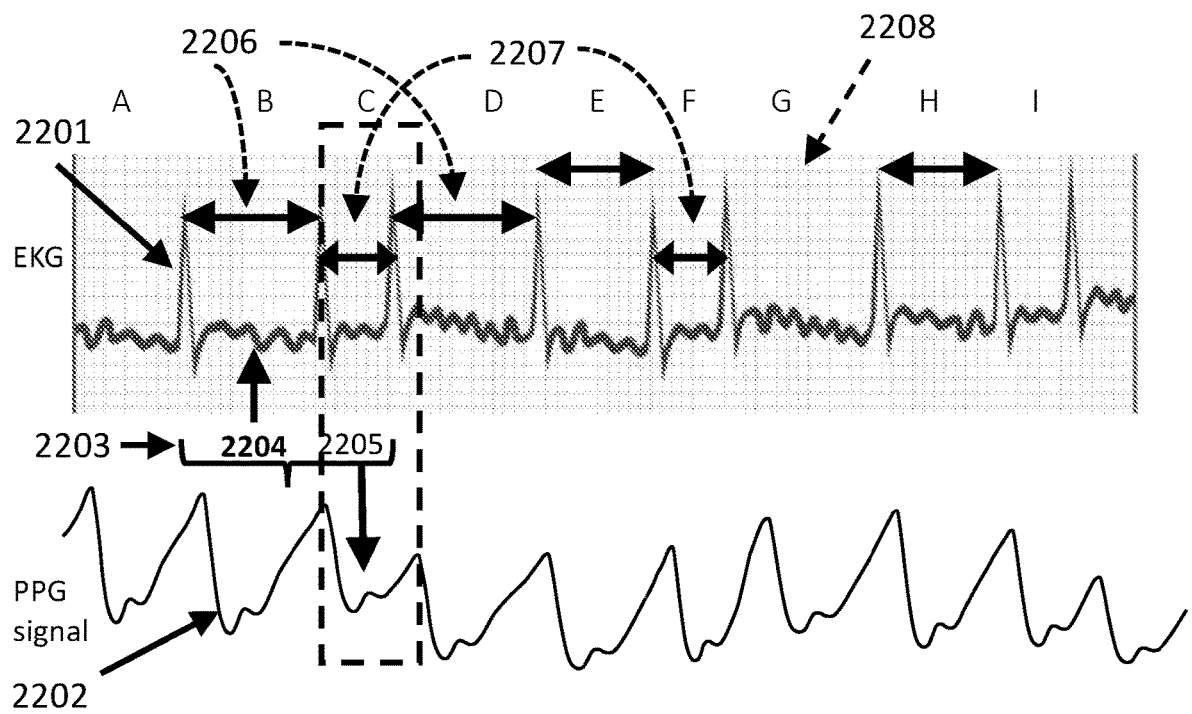
FIG. 22 illustrates a time-correlated comparison of EKG and PPG signals showing the relationships in creation of two-beat dependencies, showing "prior R-to-R" (a.k.a. "n−1 R-to-R").

Two Beat Dependency Selection and Analysis:

2-beat dependency selection for a longer train of pulses in atrial fibrillation (yielding random R-to-R duration) is shown in FIG. 22. Signal from a two-electrode, single lead EKG (curve 2201) is plotted in temporal alignment with an infrared (IR) LED PPG signal (curve 2202). As the infrared wavelength has relatively equivalent absorption from venous and arterial blood, this is the better wavelength with which to select pulses for further analysis.

FIG. 22 shows the top/bottom alignment of EKG (2201) and PPG signals (2202) showing the steps in an alternative method of generating a composite PPG wave. The above EKG (2201) signal shows a series of pulses labeled A through I. Each of these pulses has a different duration, though some are closer in duration than others. 2-beat dependency ties together two successive beats, with key features being the R-to-R duration of the first beat, and the PPG signal of the second beat. This is dependency (2203) is depicted in the bracket tying together the R-to-R duration of beat "B" (2204) and the PPG signal (2205) of beat "C". Pulses B and C are analyzed together, with the R-to-R duration of B putting this 2-beat complex in the long prior (n−1) R-to-R "bin". Next, pulses C and D are considered together, with the R-to-R duration of C putting this 2-beat complex in the short prior (n–1) R-to-R bin. Next, pulses D and E are considered together, with the R-to-R duration of D putting this 2-beat complex in the long prior (n–1) R-to-R "bin" (along with complex B-C). Next, pulses E and F are considered, with the R-to-R duration of E putting this 2-beat complex in the intermediate bin. 2206 points to similar R-to-R durations, putting complexes B-C and D-E, along with H-I in the intermediate prior (n–1) R-to-R bin. 2207 points to similar short R-to-R durations, putting complexes C-D, F-G, and I-J (off page to right) into the short prior (n–1) R-to-R bin. Complex G-H (2208) goes in the long prior (n–1) R-to-R bin.

Prior-Prior R-to-R Dependency

Figure 23:
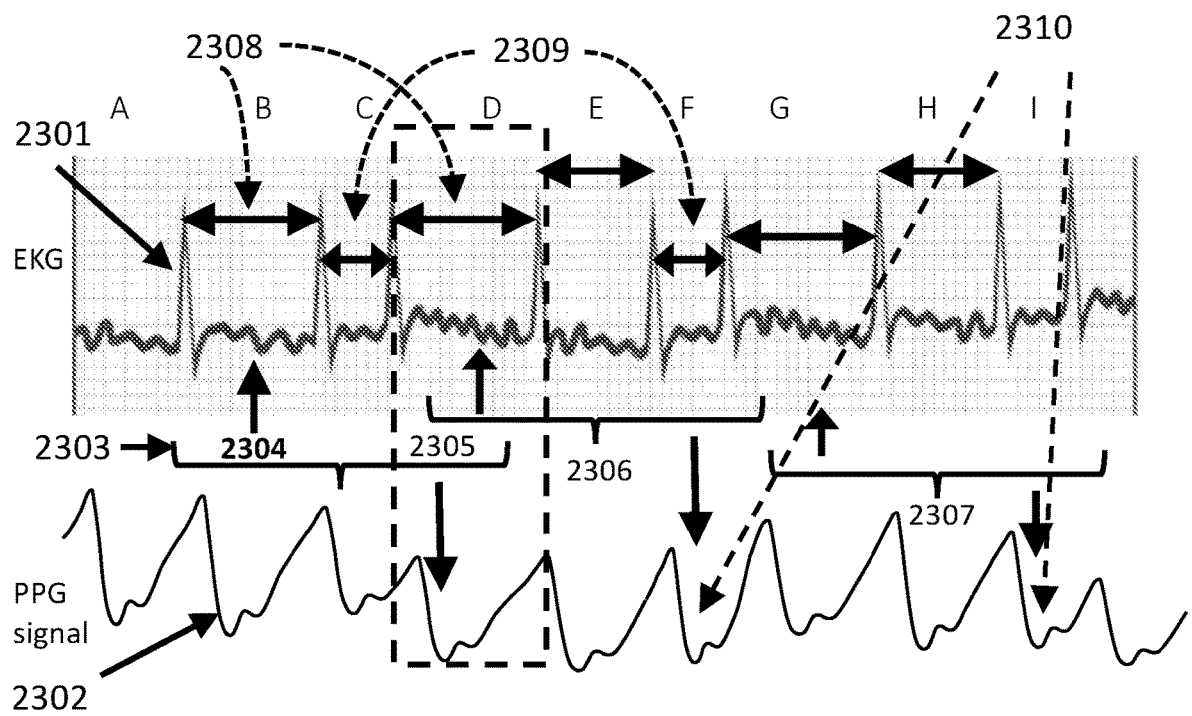
FIG. 23 illustrates a time-correlated comparison of EKG and PPG signals showing the relationships in creation of two-beat dependencies, showing "prior prior R-to-R" (a.k.a. "n−2 R-to-R").

Prior-prior R-to-R dependency selection for a longer train of pulses in atrial fibrillation (yielding random R-to-R duration) is shown in FIG. 23. Signal from a two-electrode, single lead EKG (curve 2301) is plotted in temporal alignment with an infrared (IR) LED PPG signal (curve 2302). As the infrared wavelength as relatively equivalent absorption from venous and arterial blood, this is the better wavelength with which to select pulses for further analysis.

FIG. 23 shows the top/bottom alignment of EKG (2301) and PPG signals (2302) showing the steps in an alternative method of generating a composite PPG wave. The above EKG signal 2301 shows a series of pulses labeled A through I. Each of these pulses has a different duration, though some are closer in duration than others. 2-beat dependency ties together two beats separated by a third beat, with key features being the R-to-R duration of the first beat, and the PPG signal of the beat 2 beats later. This is dependency (2303) is depicted in the bracket tying together the R-to-R duration of beat "B" (2304) and the PPG signal (2305) of beat "D". Similar dependencies are shown with brackets 2306 and 2307. Pulses B and D are analyzed together, with the R-to-R duration of B putting the arterial oxygen saturation from PPG signals of pulse D in the long n–2 R-to-R "bin". Next, pulses C and E are analyzed together, with the R-to-R duration of C putting the arterial oxygen saturation from PPG signals of pulse E in the short n–2 R-to-R "bin". Next, pulses D and F are analyzed together, with the R-to-R duration of D putting the arterial oxygen saturation from PPG signals of pulse F in the long n–2 R-to-R "bin". Next, pulses E and G are analyzed together, with the R-to-R duration of E putting the arterial oxygen saturation from PPG signals of pulse G in the intermediate n–2 R-to-R "bin". Next, pulses F and H are analyzed together, with the R-to-R duration of F putting the arterial oxygen saturation from PPG signals of pulse H in the short n–2 R-to-R "bin". Next, pulses G and I are analyzed together, with the R-to-R duration of G putting the arterial oxygen saturation from PPG signals of pulse I in the long n–2 R-to-R "bin".

Thus, complexes B-D and D-F go together in the long prior-prior (n–2) R-to-R bin (2308), along with complex G-I. 2310 points to the PPG signals for F and I that will be considered similar using this analysis. Complexes C-E and F-H go together in the short prior-prior (n–2) R-to-R bin (2309), along with complex I-K (off page to right).

Top-Level Block Diagram for 2-Beat Dependency

Figure 24:
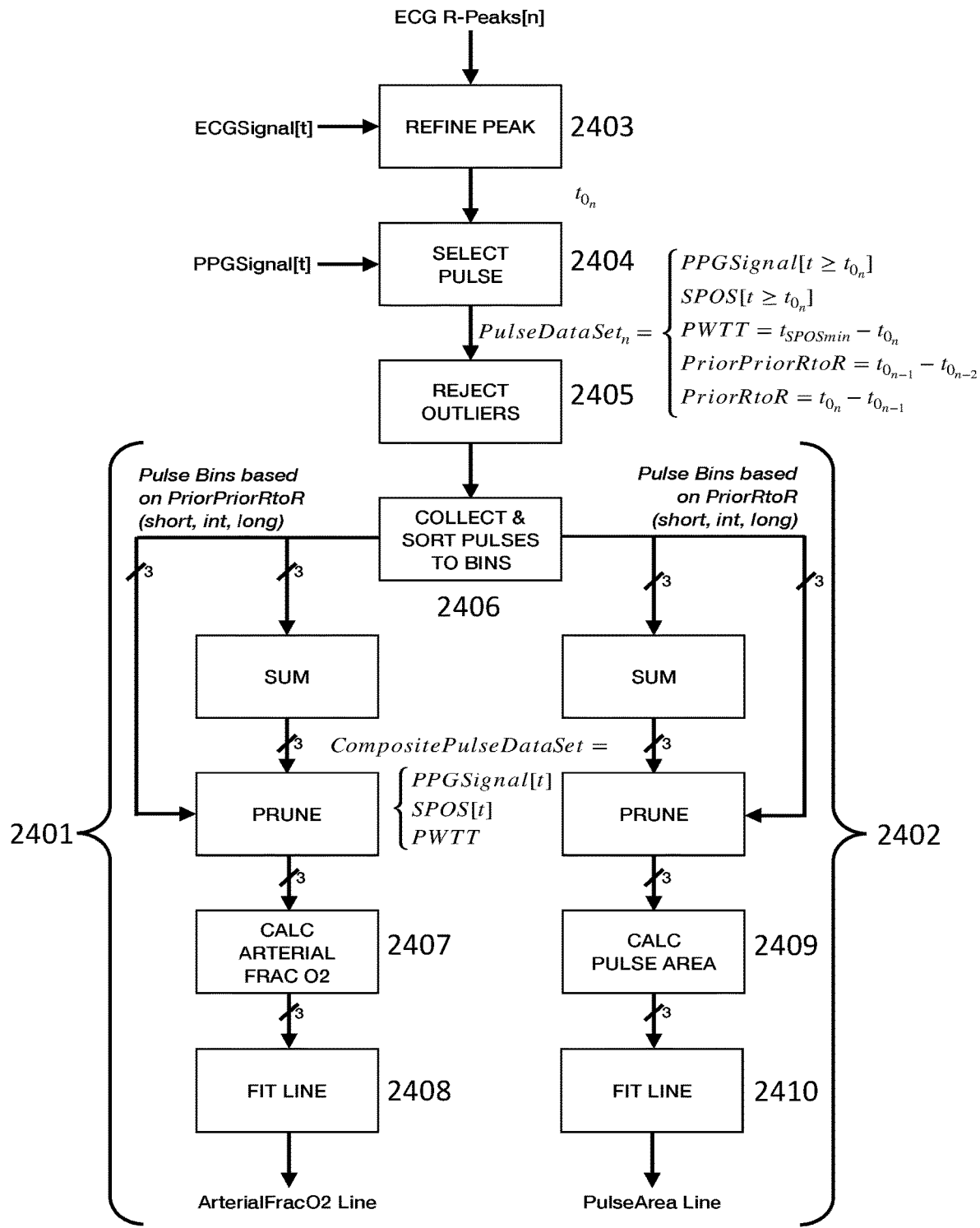
FIG. 24 is a flow diagram for the 2-beat dependency using Pulse Data Set "n" arterial oxygen saturation ("Arterial Frac $O_2$") from PPG signals with the prior-prior R-to-R duration shown in the left limb of the diagram.

The flow for the 2-beat dependency using Pulse Data Set "n" arterial oxygen saturation ("Arterial Frac $O_2$") from PPG signals and the prior-prior R-to-R duration is shown in the left limb (2401) of the block diagram of FIG. 24; the flow for the 2-beat dependency using Pulse Data Set "n" PPG signals and the prior R-to-R duration is shown in the right limb (2402) of the block diagram.

R-wave peak refinement of pulse "n" is done with curve fitting and interpolation (2403) prior to determining the n–1 R-to-R duration; then n–2 and n–1 R-to-R duration for Pulse Data Set "n" are incorporated into Pulse Data Set "n" (2404). PPG signals are gathered, and a process of outlier rejection is carried out (including but not limited to data determined to be corrupted using accelerometer input, as well as cross-checking with multiple LED PPG sensors, 2405). Once the PPG signals of the current Pulse Data Set have been selected, the Pulse Data Set is considered together with all available prior Pulse Data Sets and their PPG signals (each of which is associated with a prior (n–1) R-to-R duration and prior-prior (n–2) R-to-R duration).

At this point two different analyses are done (2406).

In the left limb (2401), the available Pulse Data Sets are sorted by prior-prior R-to-R into short, intermediate, and long "bins", with dynamic boundary adjustment ensuring relatively equal numbers across bins. After available Pulse Data Sets are allocated to the given bins, an initial Composite Pulse Data Set is constructed by summing each of the Pulse Data Set PPG signals together. Subsequently, a pruning loop is carried out for each bin to out to weed out Pulse Data Sets with noisy or otherwise aberrant PPG signals that made it through the coarser outlier rejection. For each Pulse Data Set in the bin, and for each wavelength in the Pulse Data Set, the PWTT for the wavelength is compared against the PWTT using SPOS for the wavelength for the Composite Pulse Data Set (aggregate of all the pulses). If the PWTT of two of the current three wavelengths (red, green, IR) are within a certain threshold (currently 15%) of the corresponding wavelength PWTT from the Composite Pulse Data Set, the Pulse Data Set is left in the composite. If not, the Pulse Data Set is rejected ("pruned") and the process is run again with the remaining Pulse Data Sets. Pruning a Pulse Data Set removes it from the bin and subtracts it from the Composite Pulse Data Set. If the number of Pulse Data Sets falls below a specified threshold for the number in the bin (good results have been obtained with numbers down to 4), then an additional Pulse Data Set is added prior to reporting any results. This algorithm is seen in FIG. 25. When the Composite Pulse Data Set PPG signals for all 3 bins has been successfully pruned, an arterial oxygen saturation calculation is done on each of the set of Composite Pulse Data Set PPG signals (2407), resulting in a trio of arterial saturation to prior-prior R-to-R duration pairs. Finally, a line representing arterial saturation vs prior-prior R-to-R is fit to the 3 data pairs (2408).

Returning to the box at the branching point left/right ("COLLECT & SORT PULSES TO BINS", 2406), all the available Pulse Data Sets are once again considered, this time with regard to the prior R-to-R duration. Following the right limb (2402), the available Pulse Data Sets are sorted by prior R-to-R into short, intermediate, and long "bins", with dynamic boundary adjustment ensuring relatively equal numbers across bins. After available Pulse Data Sets are allocated to the given bins, an initial Composite Pulse Data Set is constructed by summing each of the PPG signals together. Subsequently, the same pruning loop carried out on the left limb is then applied to each Pulse Data Set in each bin on the right limb. A pruned Pulse Data Set is removed from the bin and subtracted it from the Composite Pulse Data Set. When the Composite Pulse Data Set PPG signals for all 3 bins has been successfully pruned, the inferior-most area of the PPG curve (corresponding to the arterial peak pulse area) is calculated for each bin (2409), yielding a trio of pulse area to prior R-to-R duration pairs. Finally, a line representing Pulse Area vs prior R-to-R is fit to the 3 pairs (2410). It is to be understood that SPOS signals that are based on PPG signals, and not composite SPOS signals, can be used for the various forms of pruning as described herein.

Figure 26:
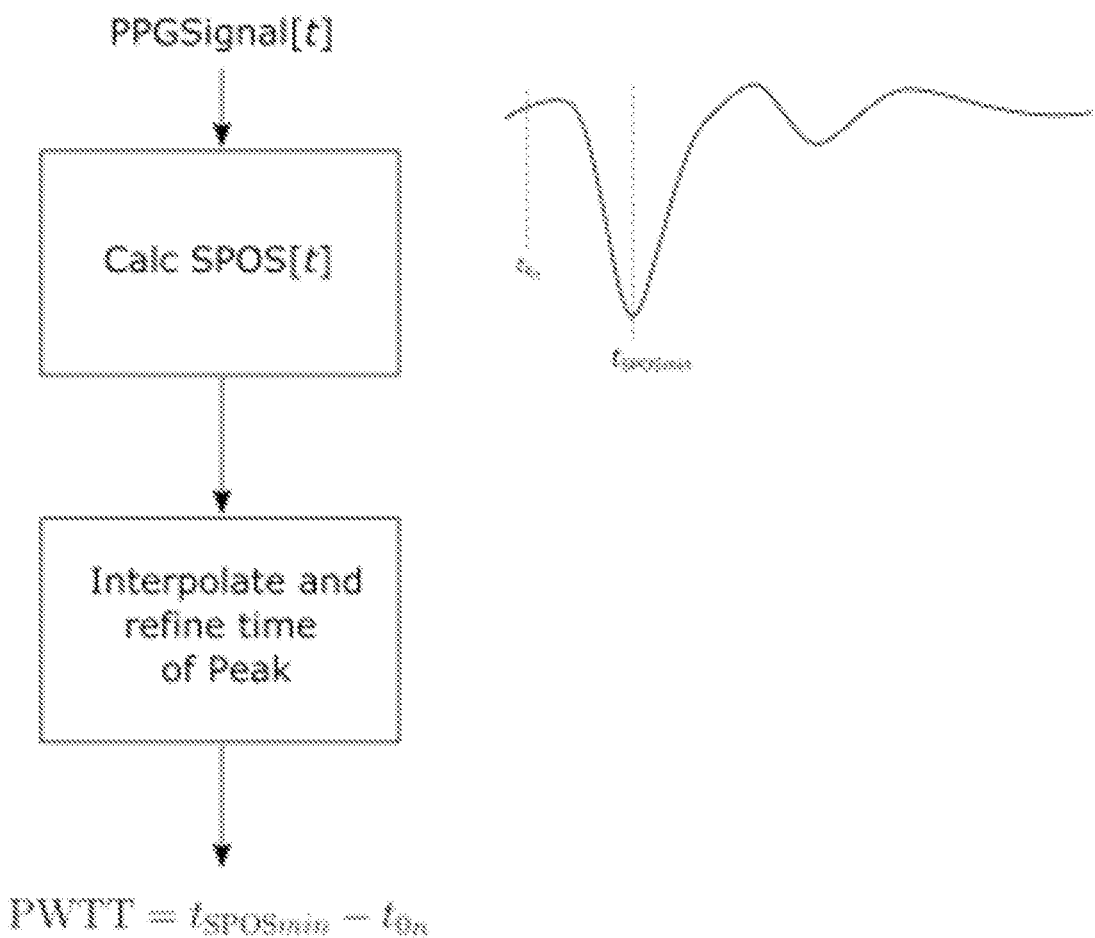
FIG. 26 illustrates the derivation of the Pulse Wave Transit Time (PWTT).
Figure 27:
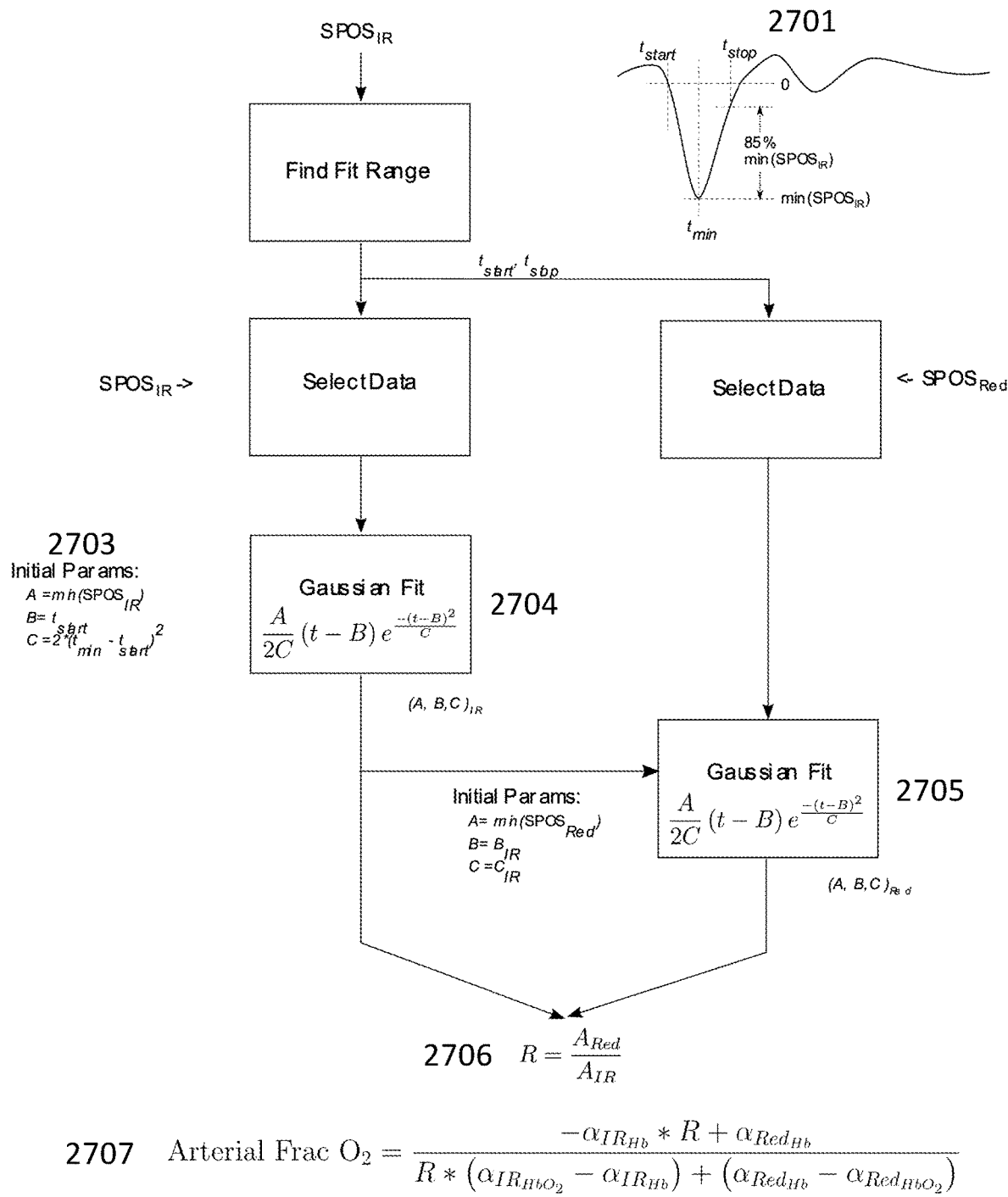
FIG. 27 shows a flow diagram for an exemplary method of calculating arterial oxygen saturation in accordance with the present system.

FIG. 26 shows the derivation of the Pulse Wave Transit Time (PWTT). This is done using the Signal Prime Over Signal (SPOS(t)) curve for each wavelength PPG signal(t), together with interpolation and (negative) peak refinement. FIG. 27 shows the flow diagram for the arterial oxygen calculation used in the system. Note that a one-sided Gaussian derivative is used to better fit the resultant Composite Pulse Data Set PPG signals (2701), as noted in the introduction to the detailed description of the invention. The system uses a fit window as seen in FIG. 20, fitting from the infrared (IR) wavelength SPOS curve crossing from positive to negative down to the negative spike, then up to 15% of the distance from the minimum to zero (the x-axis).

Parameters A, B, C for the Gaussian curve are found using initial best guess values (derived from time of first positive to negative crossing, time of minimum, and negative magnitude, 2703), then using a non-linear least square error fitting (2704). Following this, the resultant Gaussian is fit to the red wavelength SPOS curve (2705), allowing only the magnitude A to vary. An R value for $A_{Red}/A_{IR}$ is then calculated (2706), and put into the standard arterial oxygen saturation fraction equation (2707).

Figure 28:
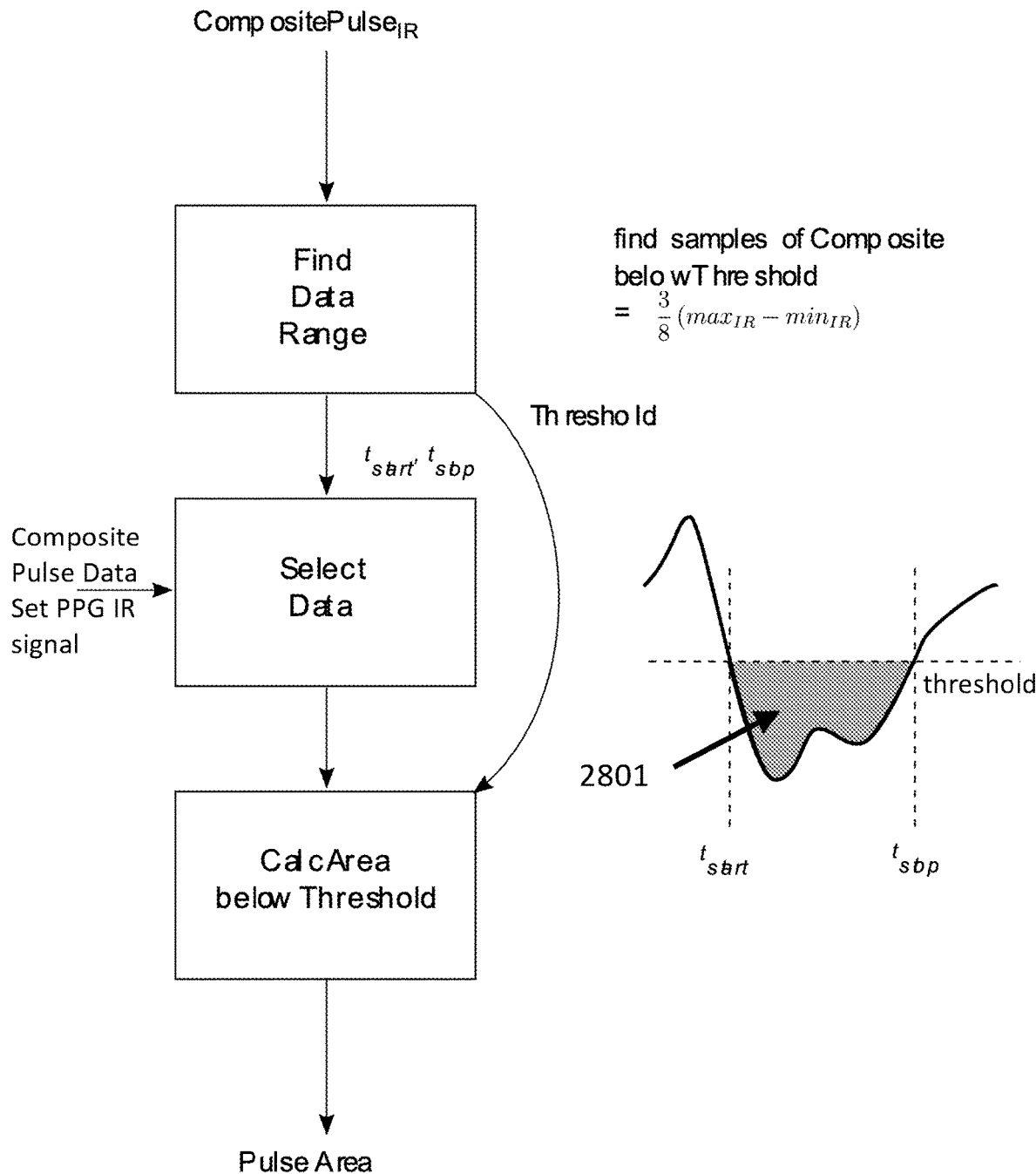
FIG. 28 shows a flow diagram for an exemplary method of calculating pulse area in accordance with the present system.

FIG. 28 shows the calculation of the pulse area (2801). This calculation uses the Composite Pulse Data Set PPG signal for the infrared (IR) wavelength. Because the absorption coefficients for oxygenated hemoglobin and deoxygenated hemoglobin are nearly the same for IR, the IR PPG signal corresponds to the total blood flow better than the red wavelength. Calculating the area at the bottom of the IR curve (corresponding to the arterial pulse peak) thus measures how rounded the arterial pulse is at the peak. Various criteria can be used, though the current criteria uses the area formed by the curve below 3/8 of the maximum—minimum IR PPG value.

Figure 29:
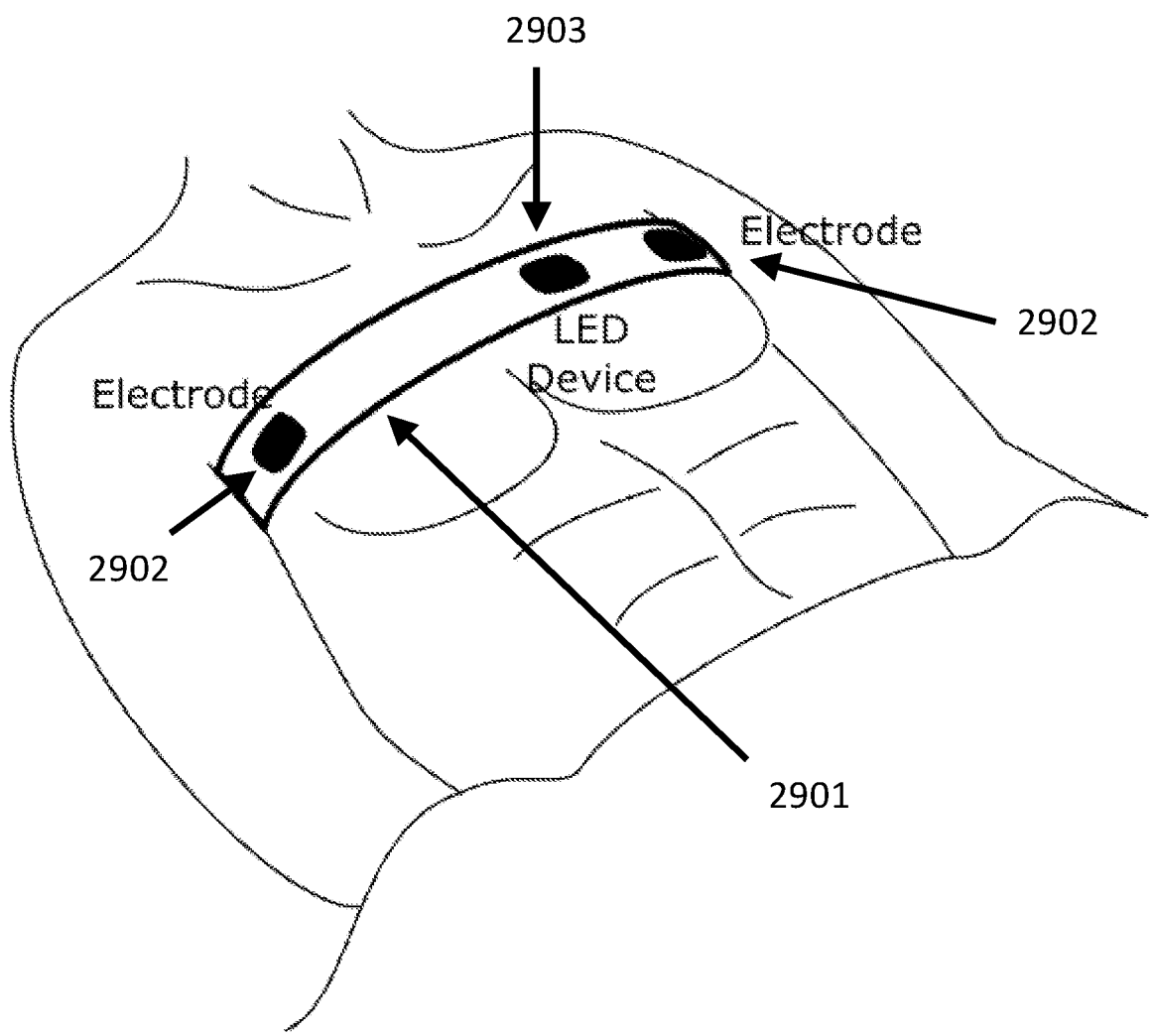
FIG. 29 illustrates an exemplary embodiment of the present system disposed in a chest strap.

System Operation:

Operational alternative options are presented in the various exemplary embodiments of the present system, below. It is to be understood that the present system can be embodied in any of the systems described herein, and that the present system is not limited solely to the various exemplary embodiments described below:

FIG. 29 illustrates use of a chest strap (2901) across the chest, with incorporated electrodes (2902) contacting the left and right chest, and LED device with detector (2903).

Figure 30:
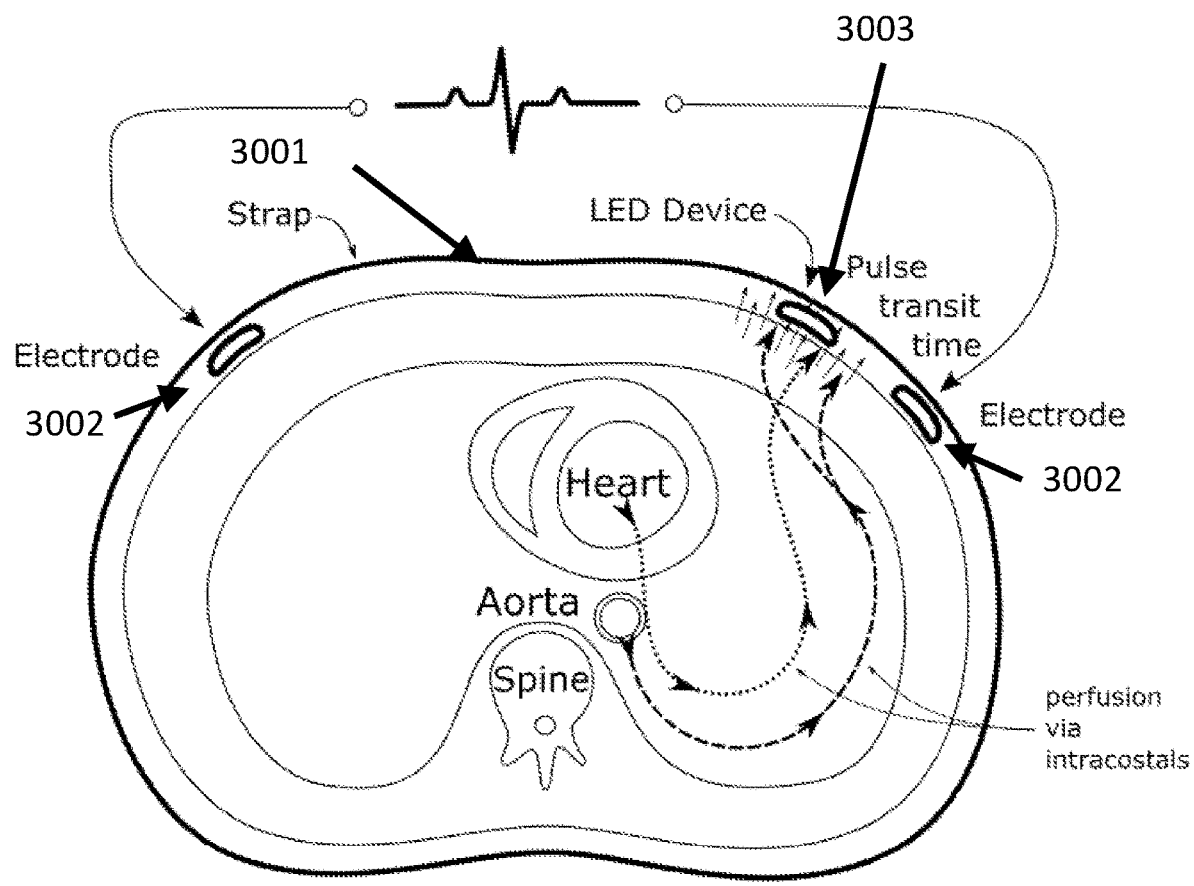
FIG. 30 is a sectional view through the patient corresponding to FIG. 29.

FIG. 30 illustrates the cross section of a chest strap (3001) across the chest, with incorporated electrodes (3002) contacting the left and right chest, and LED device with detector (3003).

Figure 31:
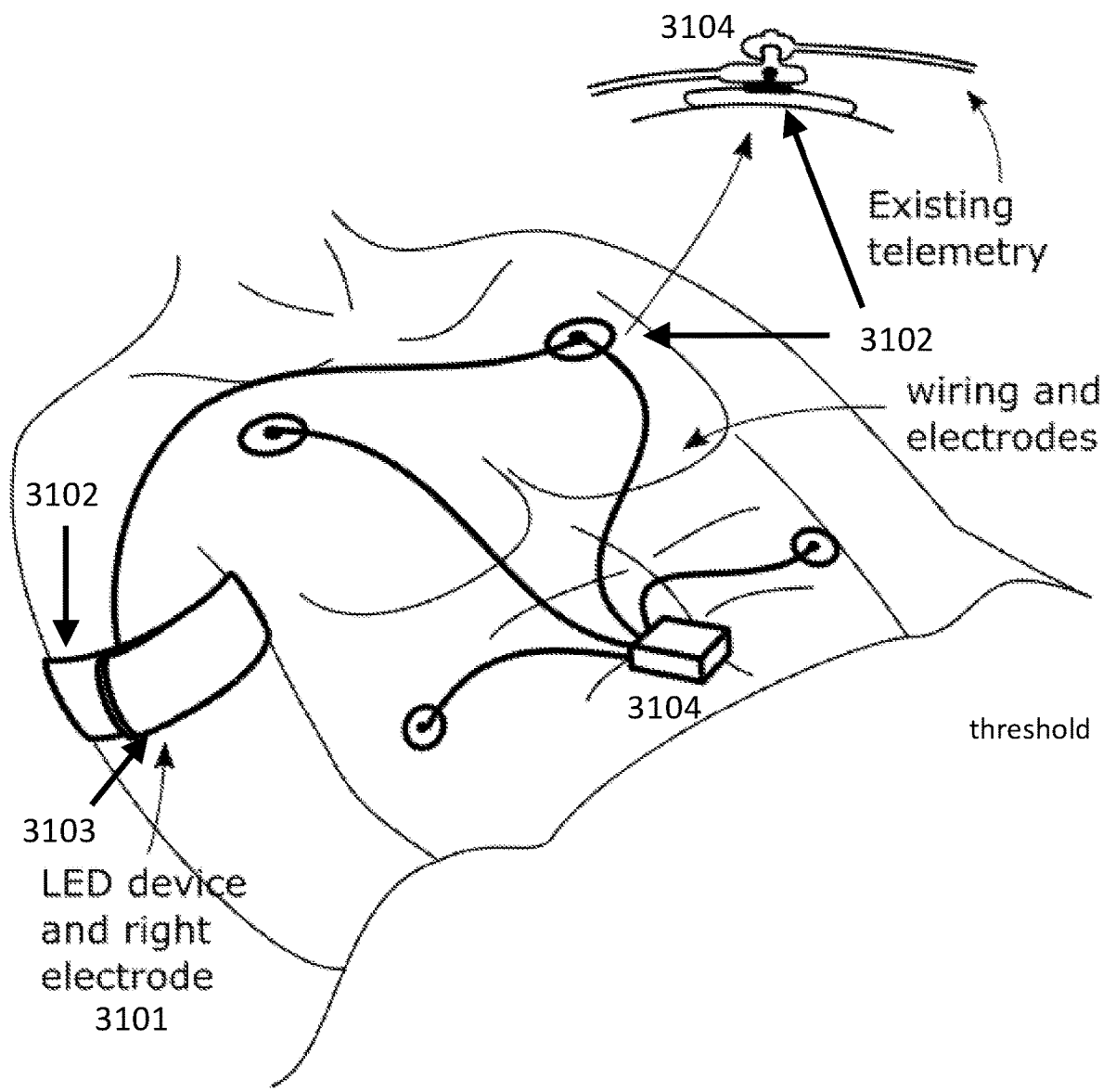
FIG. 31 illustrates an exemplary embodiment of the present system incorporating a bicep strap with an electrode extending therefrom.

FIG. 31 illustrates the use of a bicep strap (3101), with incorporated electrode (3102) and LED device with detector (3103). A second electrode piggybacks off existing telemetry wiring (3104).

Figure 32:
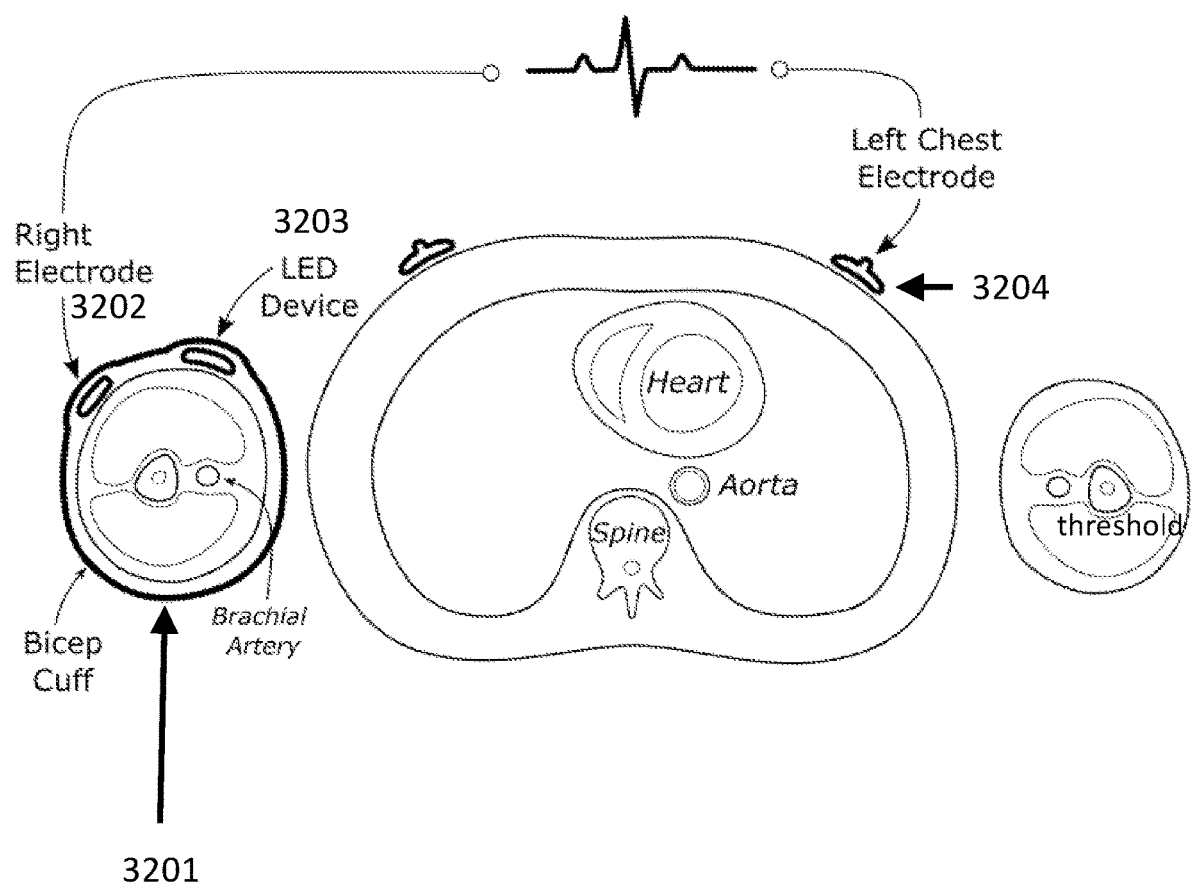
FIG. 32 is a sectional view through the patient corresponding to FIG. 31.

FIG. 32 illustrates a cross section of a bicep strap (3201), with incorporated electrode (3202) and LED device with detector (3203). A second electrode piggybacks off existing telemetry wiring (3204).

An advantage of a chest or arm strap or band is that the band/strap provides a normal force on the LED of the PPG sensor to get a good signal off the chest wall. In aspects where a chest or arm strap is used, optional "traction" may also be provided on the inside of the strap, similar to the silicone/adhesive bead that is found on the inside of standard bike shorts to keep the legs from riding up.

Appendix a: Cardiovascular Physiology Background

Cardiovascular health is essential to overall health and optimal hydration only makes sense within the context of the cardiac function of the given patient. There are many aspects to this optimal functioning, and a full description is beyond the scope of the background needed here. However, an essential part of that optimal functioning is the ability to simultaneously maintain the circumstances of minimal interstitial fluid within the lungs, and high arterial flow to the capillary networks of the body. While some tissues and organs have a degree of reserve in the event of temporary decrease in perfusion, the heart, brain, and kidneys do not. Adequate arterial pressure and volume (the result of ventricular contraction, or systole) is needed to deliver against gravity to the brain, and provide sufficient pressure for the "coffee filters" of the kidney to remove waste products. The balance is maintained by keeping the pulmonary system (the portion of the circulatory system between the right heart and the left heart, wherein blood flow through the lungs) pressures low relative to systemic arterial (the circulatory system supplying the body with oxygen gathered from the lungs) pressures. Drastically simplifying the situation, the lungs must be kept "dry" while the kidneys are kept "wet", all while maintaining adequate intravascular fluid needed to keep the flow of nutrients to tissues and removal of wastes from tissues. In normal health the greater concern is too little intravascular fluid than too much. Low blood pressure, high heart rate, lightheadedness, and declining and darkening urine output can be a tip off to a low volume state. Even in the state of healthy organs, additional information may sometimes be useful, as when an individual is approaching a state of dangerous dehydration unawares; as when an individual is under anesthesia and/or post-surgical, or in the setting of acute trauma.

However, in the situation of impaired cardiovascular function, or reduced ability to retain arterial blood due to leaky capillaries (malnutrition, acute sepsis), the risk of intravascular dehydration is complicated by the increased problem of excess body fluid, especially when that fluid builds up in the lungs. One can view the situation of the lungs much like a boat in water. Any boat, no matter how sound, will accumulate water, and needs bailing on a regular basis. When the left heart is functioning normally, it provides this needed bailing action; when left heart function is impaired for any reason, interstitial lung fluid begins to rise.

Cardiac output is the product of how much blood is ejected from the heart each beat (stroke volume) times the number of beats per minute. However, the stroke volume in turn is dependent on a number of factors (adrenergic state, prior heart insults, intravascular fluid status, etc.), including the heart rate in certain regimes.

Optimal function of the heart requires a balance between relaxation (diastole) of the heart muscle and contraction (systole). The Frank-Starling curve (FIG. 3) describes the relationship between heart output that occurs during systole (contraction) and the filling of the heart that occurs in diastole (relaxation). As seen in the figure, even with normal function there is a point of peak output; however, with heart pump failure the point beyond which more end-diastolic (end-relaxation), pre-systolic (pre-contraction) filling yields diminishing returns (dashed line) is more easily encountered. Prior to that point, though, more fluid is better. The clinical problem is knowing how close to the peak one is, because the scenario is different depending on the curve (e.g. normal versus heart failure).

Venous return to the heart is generally harder to measure. Modeling the circulatory system as a closed system have traditionally (and somewhat confusingly) yielded curves of venous return as in FIG. 33. These curves have used right atrial pressure (the clinically measurable quantity) as the x-axis overlaid with Frank-Starling curves (3301, 3302, 3303) using left ventricular filling/distension (the clinically measurable quantity) as the x-axis. Venous return curves (3304, 3305, 3306) are shown. The healthy, at rest situation is represented by the Frank-Starling curve 3301 and venous return curve 3304. Venous return curves have a peak magnitude equal to that of the Frank-Starling curve. This is due to the requirement that, on average, there must be conservation of fluid. The intersection of the two curves (3307) identifies the cardiovascular state in resting normal health, much as a sales-price point on a graph in microeconomics is identified by the intersection of supply and demand curves. About this point, perturbations of left ventricular output will occur with variation in cardiac relaxation times (and thus filling time and thus end-diastolic volume) leading up to left ventricular contraction. In doing so, the ventricle will traverse up and down the Frank-Starling curve 3301 about the equilibrium/operating point 3307. Venous return will also oscillate/vary, along the venous return curve 3304, oscillating about the equilibrium/operating point as well. This then will form the basis of the cardiovascular assessment made possible by this system.

Figure 33:
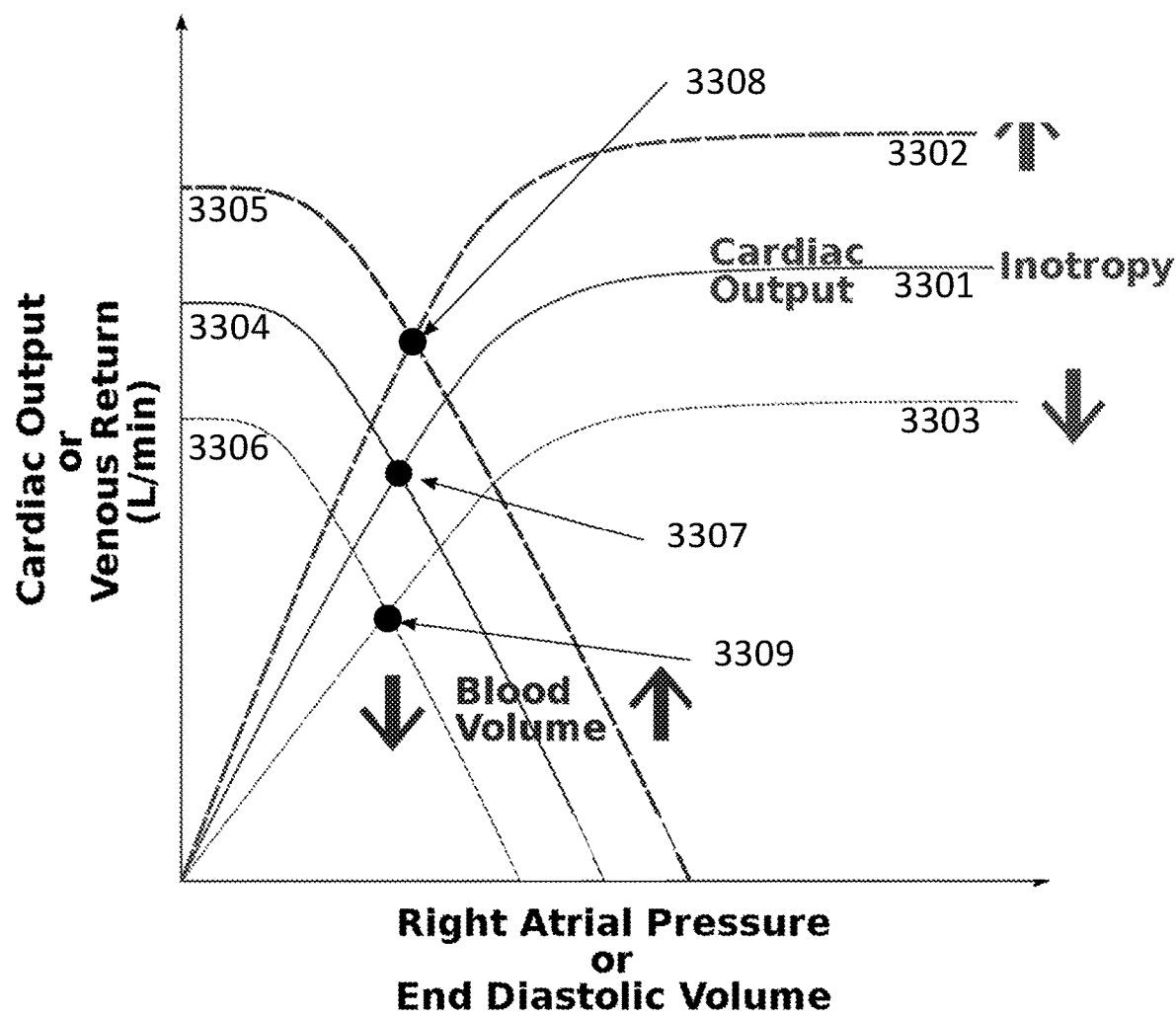
FIG. 33 is an illustration of Frank-Starling and venous return curves, with the intersection of the curves being an indication of cardiovascular state.

Also seen in FIG. 33 are the Frank-Starling curve 3302 and venous return curve 3305 reflecting health exercise (increase in inotropy, or myocardial contractility from baseline, and decreased pulmonary vascular resistance from baseline). A new operating point 3308 results. Also shown in the situation of physiologic stress, with decreased myocardial contractility seen by a lowered Frank-Starling curve 3303 and a corresponding new venous return curve 3306. This results in a new operating point with decreased cardiac output (3309).

When lung interstitial fluid increases, it interferes with the ability of hemoglobin in red blood cells to load up with oxygen, and for carbon dioxide to diffuse out of the blood traversing the capillaries surrounding the alveoli, the end air sacs in the lungs where gas exchange occurs. Fluid can fill the alveoli, further impairing the lung function. As "back pressure" rises, signs of fluid overload within the lungs can be seen, such as decreased exercise tolerance, then difficulty breathing at rest. Characteristic sound of fluid within the lungs known as "rales" can be heard on auscultation (listening with a stethoscope). Eventually the fluid backs up beyond the right heart to the level of the venous system. Signs of increased jugular pulsations are seen in the acute phase. Tissue swelling (known as edema) is seen as the situation progresses.

The more common cause of the above situation is that of chronic congestive heart disease, though all these findings can and will be seen in the situation of acute onset such as heart attack, acute pulmonary thrombosis, acute heart failure from sepsis or shock, or acute myocarditis, now recognized as a not uncommon complication of Covid-19. The problem for management is that the need to support adequate intraarterial volume for the brain and kidneys remains despite the dysfunction affecting the lungs and oxygenation. When this volume falls precipitously, the body knows to protect the brain, and therefore the kidneys are left vulnerable. Thus, the clinical situation often comes down to finding the balance between withholding fluid (or forcing fluid off the body) to protect the lungs versus giving fluid to support the kidneys. The additional wrinkle is that while excess fluid on the lungs causes sometimes severe discomfort, and the symptoms of kidney acute failure are usually not noxious, the mortality of acute kidney failure (AKI or acute kidney injury) is far higher than acute pulmonary edema. The result is that far too many doctors and nurses under-resuscitate in the setting of complicated or conflicting findings; meaning that they choose to protect the lungs instead of the kidneys when they should actually favor the kidneys due to the larger but invisible danger kidney injury represents.

The most accessible clinical tools by which to assess cardiovascular status are: clinical findings (presence/absence of edema, crackles on lung examination, elevated venous pulsations, etc.), patient symptoms, EKG, vital signs (blood pressure, heart rate, respiratory rate, temperature), oxygen saturation by standard oximetry, and urine output. Less accessible but still available tools are central venous ultrasound (often more available in the intensive care unit or emergency department) and echocardiogram—though the latter often takes hours to be ordered, done, and then interpreted. It also requires the wheeling of a desktop-sized monitor to the bedside and a technician to carry out the 30 to 45 minute test, as well as a cooperative patient. And echocardiography cannot be done on a prone (lying face down) patient (nor can central venous ultrasound). Prone positioning is used in respiratory failure to better aerate the posterior aspects of the lungs, though in such patients (often on ventilators) there is no access to the anterior chest. Neither system (echocardiogram or central venous ultrasound) is likely to be used on a patient in infection isolation. An echocardiogram additionally costs $800-1200 or more, and as noted above is not point-of-care (central venous ultrasound is billed at around $500). The Cheetah Nicom® Starling system made by Cheetah Medical of Newton Center, Massachusetts, is newer, less cumbersome, but still requires significant operator training, and is both expensive and not handheld. Data with the Cheetah Nicom® Starling system does seem encouraging, though, and validates that better knowledge of intravascular fluid status saves lives and money.

The best information regarding cardiac function and intravascular fluid is obtained with a Swan-Ganz catheter. This is a catheter inserted into the jugular or subclavian vein and threaded through the right heart into the lungs, but requires a minor surgical procedure to be placed, introduces serious risk of bleeding and infection. Moreover, there is the risk of "dropping a lung" if the lung cavity is punctured. Line sepsis (bacterial blood stream infection related to catheter placement) introduces significant risk and mortality. And catheter placement is costly ($400+placement, then additional RN costs with monitoring). Since a study in the late 1990s linked use of Swan-Ganz catheters to increased mortality, even if it produced valuable clinical information, use of this catheter has been limited.

Other options such as arterial catheters to directly monitor the arterial pressure wave, or central venous pressure monitors share many of the same risks as the Swan-Ganz catheter.

What is claimed is:

1. A computer logic system for and analyzing a PPG signal and an EKG signal, wherein the computer logic system is configured to:
obtain (a) the PPG signal from a device that includes at least on PPG sensor mounted thereon for measuring the person's PPG signal at multiple wavelengths of light, and (b) the EKG signal from a plurality of electrodes configured to be attached to the person;

segment the PPG signal into a series of PPG signal segments based upon features in the identified cardiac cycles, sort the PPG signal segments into a plurality of bins, wherein a first set of PPG signal segments are sorted into a first plurality of bins based upon a similarity in durations of prior R-to-R cardiac cycles, and a second set of PPG signal segments are sorted into a second plurality of bins based upon a similarity in durations of prior-prior R-to-R cardiac cycles, generate a composite signal for each of the first and second pluralities of bins comprising a system for summing or averaging the PPG signal segments in the bin, generate a composite Signal Prime Over Signal (SPOS) for each of the composite signals comprising a system for calculating a derivative of the composite signal and normalizing the derivative of the composite signal by the composite signal itself, measure a person's relative hydration level by detecting a change in the shape of at least one of the composite SPOS generated from the first plurality of bins and the composite SPOS generated from the second plurality of bins; and output to a display device a treatment recommendation based on the person's relative hydration level, wherein the treatment recommendation is at least of a positional change, giving further fluid, holding fluid, removing fluid, or giving diuretics.

2. The system of claim 1, wherein comparing the composite signals generated from bins on the basis of the prior R-to-R cardiac cycles against the composite signals generated from bins the basis of the prior-prior R-to-R cardiac cycles comprises:

plotting a first line representing left ventricular output with arterial pulse shape as a function of prior R-to-R, the first line being based upon values of the composite signals generated from prior R-to-R cardiac cycles, plotting a second line representing venous return with arterial hemoglobin oxygen saturation as a function of prior-prior R-to-R, the second line being based upon the composite signals generated from prior-prior R-to-R cardiac cycles, and determining an intersection point of the first and second lines as a metric of a person's relative hydration level.

3. The system of claim 1, wherein comparing the composite signals generated from bins on the basis of the prior R-to-R cardiac cycles against the composite signals generated from bins the basis of the prior-prior R-to-R cardiac cycles comprises:

calculating a first relationship representing left ventricular output with arterial pulse shape as a function of prior R-to-R, the first relationship being based upon values of the composite signals generated from prior R-to-R cardiac cycles, calculating a second relationship representing venous return with arterial hemoglobin oxygen saturation as a function of prior-prior R-to-R, the second relationship being based upon the composite signals generated from prior-prior R-to-R cardiac cycles, and comparing the first and second relationships as a metric of a person's relative hydration level.

4. The system of claim 1, wherein measuring a person's hydration level detects changes in the shape of a composite signal measured at an infrared wavelength of light.

5. The system of claim 4, wherein detecting changes in the shape of a composite signal measured at an infrared wavelength of light comprises correlating intra-arterial fluid volume to an area under the curve of the composite signal measured at an infrared wavelength of light.

6. The system of claim 1, wherein the computer logic system is further configured to:

determine Pulse Wave Transit Time by determining a time interval between an onset of an R-wave complex in the cardiac cycle and the occurrence of a shape feature in the composite SPOS.

7. The system of claim 6, wherein the shape feature in the composite SPOS is a minimum of the composite SPOS.

8. The system of claim 1, wherein the device is a hand-held device with the at least one PPG sensor mounted thereon and a plurality of electrode wires extending therefrom.

9. The system of claim 8, wherein the device is a hand-held device with the at least one PPG sensor mounted thereon and at least one of the plurality of electrodes mounted thereon.

10. The system of claim 8, wherein an optical waveguide is interposed between the at least one PPG sensor on the device and the person's skin.

11. The system of claim 1, wherein the device is positioned within a strap or band disposed around the person's chest or limb such that the at least one PPG sensor and the plurality of electrodes are disposed within the strap or band disposed around the person's chest or limb.

12. The system of claim 1, wherein the device is a patch with the at least one PPG sensor and at least one of the plurality of electrodes positioned therein.

13. The system of claim 1, wherein the computer logic system is positioned within the device such that the composite signals are generated within the device, and wherein the computer logic system comprises:

a data transmission system for transmitting one or both of:
the composite signals to a remote computer system for analysis, or
measured PPG and EKG signals to a remote computer system for analysis.

14. The system of claim 1, wherein generating a composite signal for each of the plurality of bins comprises a system for removing aberrant PPG signal segments from the calculation of the composite signal.

15. The system of claim 1, wherein generating a composite signal for each of the sets comprises a system for iteratively re-calculating the composite signal, by:

comparing a SPOS of each of the PPG signal segments used to calculate the composite signal against the composite SPOS of the calculated composite signal,
removing outlier PPG signal segments,
re-calculating the composite signal with the outlier PPG signal segments removed, and
repeating the iteration until there are no more outlier PPG signal segments.

16. The system of claim 15, wherein outlier PPG signal segments are identified by comparing PPG signal segments measured at different wavelengths of light against the calculated composite signal.

17. The system of claim 1, wherein the computer logic system is further configured to:

calculate arterial hemoglobin oxygen saturation by comparing composite SPOS signals measured at different wavelengths of light.

18. A method for receiving and analyzing a PPG signal and an EKG signal, the method comprising:

obtaining, via a computer logic system, (a) the PPG signal from a device that includes at least on PPG sensor mounted thereon for measuring the person's PPG signal at multiple wavelengths of light, and (b) the EKG signal from a plurality of electrodes coupled to the person;

identifying, via the computer logic system, cardiac cycles in the EKG signal;

segmenting, via the computer logic system, the PPG signal into a series of PPG signal segments based upon features in the identified cardiac cycles, sorting, via the computer logic system, the PPG signal segments into a plurality of bins, wherein a first set of PPG signal segments are sorted into a first plurality of bins based upon a similarity in durations of prior R-to-R cardiac cycles, and a second set of PPG signal segments are sorted into a second plurality of bins based upon a similarity in durations of prior-prior R-to-R cardiac cycles, generating, via the computer logic system, a composite signal for each of the first and second pluralities of bins by summing or averaging the PPG signal segments in the bin, generating, via the computer logic system, a composite Signal Prime Over Signal (SPOS) for each of the composite signals by calculating a derivative of the composite signal and normalizing the derivative of the composite signal by the composite signal itself, measuring, via the computer logic system, a person's relative hydration level by detecting a change in the shape of at least one of the composite SPOS generated from the first plurality of bins and the composite SPOS generated from the second plurality of bins; and outputting, to a display device, a treatment recommendation based on the person's relative hydration level, wherein the treatment recommendation is at least of a positional change, giving further fluid, holding fluid, removing fluid, or giving diuretics.

* * * * *